(12) United States Patent
Kalpana

(10) Patent No.: US 7,326,416 B2
(45) Date of Patent: Feb. 5, 2008

(54) INHIBITION OF HIV-1 VIRION PRODUCTION BY A TRANSDOMINANT MUTANT OF INTEGRASE INTERACTOR 1(INI1)/HSNF5

(75) Inventor: Ganjam V. Kalpana, Yonkers, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 580 days.

(21) Appl. No.: 10/624,080

(22) Filed: Jul. 21, 2003

(65) Prior Publication Data

US 2004/0091487 A1 May 13, 2004

Related U.S. Application Data

(60) Provisional application No. 60/397,305, filed on Jul. 19, 2002.

(51) Int. Cl.
*A61K 39/42* (2006.01)
(52) U.S. Cl. ............... 424/160.1; 530/388.35
(58) Field of Classification Search .............. None
See application file for complete search history.

(56) References Cited

U.S. PATENT DOCUMENTS 5,872,213 A * 2/1999 Goff et al. ............. 530/350

OTHER PUBLICATIONS

Biegel, J.A. et al., "Germ-line and acquired mutations of INI1 in atypical teratoid and rhabdoid tumors"; Cancer Res., vol. 59, pp. 74-79 (1999).
Bukovsky, A. et al., "Lack of integrase can markedly affect human immunodeficiency virus type 1 particle production in the presence of an active viral protease"; J. Virol., vol. 70, No. 10, pp. 6820-6825 (1996).
Cheng, S.W. et al., "c MYC interacts with INI1/hSNF5 and requires the SWI/SNF complex for transactivation function"; Nat. Genet., vol. 22, No. 1, pp. 102-105 (1999).
Engleman, A. et al., "Multiple effects of mutations in human immunodeficiency virus type 1 integrase on viral replication"; J. Virol., vol. 69, No. 5, pp. 2729-2736 (1995).
Fletcher, T.M. et al. "Complementation of integrase function in HIV-1 virions"; EMBO. J., vol. 16, No. 16, pp. 5123-5138 (1997).
Kalpana, G.V. et al., "Binding and stimulation of HIV-1 integrase by a human homolog of yeast transcription factor SNF5"; Science, vol. 266, pp. 2002-2006 (1994).
Kingston, R.E. et al., "ATP-dependent remodeling and acetylation as regulators of chromatin fluidity"; Genes & Dev., vol. 13, pp. 2339-2352 (1999).
Leavitt, A.D., et al., "Human Immunodeficiency Virus Type 1 Integrase Mutants Retain In Vitro Integrase Activity yet Fail to Integrate Viral DNA Efficiently during Infection"; J. Virol., vol. 70, No. 2, pp. 721-728 (1996).

Lee, D. et al., "Interaction of E1 and hSNF5 proteins stimulates replication of human papillomavirus DNA"; Nature, vol. 399, pp. 487-491 (1999).
Lee, D. et al., "SWI/SNF complex interacts with tumor suppressor p53 and is necessary for the activation of p53 mediated transcription"; J. Biol. Chem., vol. 277, No. 25, pp. 22330-22337 (2002).
Morozov, A., et al., "Structure-function analysis of integrase interactor 1/hSNF5L1 reveals differential properties of two repeat motifs present in the highly conserved region"; Proc. Natl. Acad. Sci. USA, vol. 95, pp. 1120-1125 (1998).
Nakamura, T. et al., "Lack of infectivity of HIV-1 integrase zinc finger-like domain mutant with morphologically normal maturation"; Biochem. Biophys. Res. Commun., vol. 239, pp. 715-722 (1997).
Rozenblatt-Rosen, O., et al., "The C terminal SET domains of ALL 1 and TRITHORAX interact with the INI1 and SNR1 proteins, components of the SWI/SNF complex"; Proc. Natl. Acad. Sci. USA, vol. 95, pp. 4152-4157 (1998).
Versteege, I. et al., "Truncating mutations of hSNF5/INI1 in aggressive paediatric cancer"; Nature, vol. 394, pp. 203-206 (1998).
Wang, W. et al., "Purification and biochemical heterogeneity of the mammalian SWI-SNF complex"; EMBO. J., vol. 15, pp. 5370-5382 (1996).
Wiskerchen et al., "Human immunodeficiency virus type 1 integrase: Effects of mutations on viral ability to integrate, direct viral gene expression from unintegrated viral DNA templates, and sustain viral propagation in primary cells"; J. Virol., vol. 69, No. 1, pp. 376-386 (1995).
Wu, D.Y. et al., "Epstein Barr virus nuclear protein 2 (EBNA2) binds to a component of the human SNF-SWI complex, hSNF5/Ini1"; J. Virol., vol. 70, No. 9, pp. 6020-6028 (1996).
Wu, X. et al., "Human immunodeficiency Virus type 1 integrase protein promotes reverse transcription through specific interactions with the nucleoprotein reverse transcription complex"; J. Virol., vol. 73, No. 3, pp. 2126-2135 (1999).
Yung, E. et al., "Inhibition of HIV-1 virion production by a transdominant mutant of integrase interactor 1"; Nature Med., vol. 7, No. 8, pp. 920-926 (2001).
Chin, A., "On the preparation and utilization of isolated and purified oligonucleotides." Kathrine R. Everett Law Library of the University of North Carolina, Mar. 14, 2002. (on attached CD-ROM).

* cited by examiner

*Primary Examiner*—Bruce R. Campell
*Assistant Examiner*—Michelle Horning
(74) *Attorney, Agent, or Firm*—Amster, Rothstein & Ebenstein LLP

(57) ABSTRACT

Peptides comprising an Rpt1 domain of an INI1/hSNF5 which inhibit HIV-1 production in a human cell, and vectors encoding those peptides are provided. Also provided are methods of inhibiting HIV-1 production in a cell, or spread of the HIV-1 to another cell, by treating the cells with the above peptides or vectors. Other methods of inhibiting HIV-1 production in a cell, or spread of the HIV-1 to another cell, by inhibiting production of INI1/hSNF5 are provided. Additionally, methods of determining whether a test compound inhibits HIV-1 virion production in a mammalian cell, or spread of the HIV-1 to another cell, are provided. Those methods comprise determining whether the test compound inhibits the production of INI1/hSNF5 or disrupts the interaction of HIV-1 integrase with INI1/hSNF5.

21 Claims, 10 Drawing Sheets

INHIBITION OF HIV-1 VIRION PRODUCTION BY A TRANSDOMINANT MUTANT OF INTEGRASE INTERACTOR 1(INI1)/HSNF5

CROSS-REFERENCE TO RELATED APPLICATION

This application claims the benefit of U.S. Provisional Application No. 60/397,305, filed Jul. 19, 2002, the contents of which are hereby incorporated by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. AI/GM39951 awarded by the National Institutes of Health.

BACKGROUND (1) Field of the Invention

The present invention generally relates to retrovirus inhibitors. More specifically, the invention is directed to the inhibition of HIV-1 with fragments of INI1/hSNF5 and with compounds that inhibit the production of INI1/hSNF5.

(2) Description of the Related Art

References cited

Adachi, A. et al. Generation and characterization of human immunodeficiency virus type 1 mutants. Arch. Virol. 117, 45-58 (1991).

Andrake, M. D. and A. M. Skalka, Retroviral integrase, putting the pieces together. Journal of Biological Chemistry 271(33), 19633-6 (1996).

Andrake, M. D. and A. M. Skalka, Multimerization determinants reside in both the catalytic core and C terminus of avian sarcoma virus integrase. Journal of Biological Chemistry 270(49), 29299-306 (1995).

Ansari-Lari, M. A., Donehower, L. A. & Gibbs, R. A. Analysis of human immunodeficiency virus type 1 integrase mutants. Virol. 211, 332-335 (1995).

Asante-Appiah, E. & Skalka, A. M. Molecular mechanisms of retroviral DNA integration. Antiviral Res. 36, 139-156 (1997).

Asante-Appiah, E. and A. M. Skalka, HIV-1 integrase: structural organization, conformational changes, and catalysis. Adv. Virus Res. 52, 351-69 (1999).

Babst, M., et al., Mammalian tumor susceptibility gene 101 (TSG101) and the yeast homologue, Vps23p, both function in late endosomal trafficking. Traffic 1(3), 248-58 (2000).

Bemoist and Chambon. Nature 290, 304-310 (1981).

Been and Cech. Cell 47, 207-216 (1986).

Biegel, J. A. et al. Germ-line and acquired mutations of INI1 in a typical teratoid and rhabdoid tumors. Cancer Res. 59, 74-9 (1999).

Bishop, N. and P. Woodman, ATPase-defective mammalian VPS4 localizes to aberrant endosomes and impairs cholesterol trafficking. Mol Biol Cell 11(1), 27-39 (2000).

Bouyac-Bertoia, M., et al., HIV-1 infection requires a functional integrase NLS. Mol Cell 7(5), 1025-35 (2001).

Braaten, D. and J. Luban, Cyclophilin A regulates HIV-1 infectivity, as demonstrated by gene targeting in human T cells. EMBO J. 20(6), 1300-9 (2001).

Brinster et al. Nature 296, 39-42 (1982).

Brown, P. O., et al., Retroviral integration: structure of the initial covalent product and its precursor, and a role for the viral Integrase protein. Proc. Natl. Acad. Sci. USA 86, 2525-2529 (1989).

Brown, P. O. Integration of retroviral DNA. Curr. Topics Microbiol. and Immunol. 157, 19-48 (1990).

Brown, P. Integration in Retroviruses (eds. Coffin, J. M., Hughes, S. H. & Varmus, H. E.) 161-203 (Cold Spring harbor Laboratory Press, 1997).

Bukovsky, A. & Gottlinger, H. Lack of integrase can markedly affect human immunodeficiency virus type 1 particle production in the presence of an active viral protease. J. Virol. 70, 6820-6825 (1996).

Cai, M., et al., Solution structure of the N-terminal zinc binding domain of HIV-1 integrase [published erratum appears in Nat Struct Biol 1997 October;4(10):839-40]. Nature Structural Biology 4(7), 567-77 (1997).

Cannon, P. M., Wilson, M., Byles, E., Kingsman, S. M. & Kingsman, A. J. Human immunodeficiency virus type 1 integrase: effect on viral replication of mutations at highly conserved residues. J. Virol. 68, 4768-4775 (1994).

Caplen, H. J. et al. Proc. Nat'l. Acad. Sci. USA 98, 9742-9747 (2001).

Chen, H. and A. Engelman, The barrier-to-autointegration protein is a host factor for HIV type 1 integration. Proc Natl Acad Sci USA 95(26), 15270-4 (1998).

Chen, J. C., et al., Crystal structure of the HIV-1 integrase catalytic core and C-terminal domains: a model for viral DNA binding. Proc Natl Acad Sci USA 97(15), 8233-8 (2000).

Cheng, S. W., et al., c-MYC interacts with INI1/hSNF5 and requires the SWI/SNF complex for transactivation function. Nat Genet 22(1), 102-5 (1999).

Cherepanov, P., et al., HIV-1 integrase forms stable tetramers and associates with LEDGF/p75 protein in human cells. J Biol Chem 278(1), 372-81 (2003).

Cimarelli, A. and J. Luban, Translation elongation factor 1-alpha interacts specifically with the human immunodeficiency virus type 1 Gag polyprotein. J Virol 73(7), 5388-401 (1999).

Craig, E., et al., A masked NES in INI1/hSNF5 mediates hCRM1-dependent nuclear export: implications for tumorigenesis. EMBO J 21(1-2), 31-42 (2002).

Demirov, D. G., et al., Overexpression of the N-terminal domain of TSG101 inhibits HIV-1 budding by blocking late domain function. Proc Natl Acad Sci USA 99(2), 955-60 (2002).

Desrosiers, R. C. Strategies used by human immunodeficiency virus that allow persistent viral replication. Nat. Med. 5, 723-725 (1999).

Dvorin, J. D., et al., Reassessment of the roles of integrase and the central DNA flap in human immunodeficiency virus type 1 nuclear import. J Virol 76(23), 12087-96 (2002).

Elbashir, S. M. et al. Nature 411, 494-498 (2001).

Engelman, A., F. D. Bushman, and R. Craigie, Identification of discrete functional domains of HUV-1 integrase and their organization within an active multimeric complex. EMBO J. 12, 3269-3275 (1993).

Engleman, A., Englund, G., Orenstein, J. M., Martin, M. A. & Craigie, R. Multiple effects of mutations in human immunodeficiency virus type 1 integrase on viral replication. J. Virol. 69, 2729-2736 (1995).

Esposito, D. and R. Craigie, HIV integrase structure and function. Adv Virus Res 52, 319-33 (1999).

Farnet, C. M. and F. D. Bushman, HIV-1 cDNA integration: requirement of HMG I(Y) protein for function of preintegration complexes in vitro. Cell 88, 483-92 (1997).

Fletcher, T. M., 3rd et al. Complementation of integrase function in HIV-1 virions. Embo J. 16, 5123-38 (1997).

Franke, E. K., H. E. Yuan, and J. Luban, Specific incorporation of cyclophilin A into HIV-1 virions. Nature 372 (6504), 359-62 (1994).

Gallay, P., Swingler, S., Song, J., Bushman, F. & Trono, D. HIV nuclear import is governed by the phosphotyrosine-mediated binding of matrix to the core domain of integrase. Cell 83, 569-76 (1995).

Gallay, P., et al., Role of the karyopherin pathway in human immunodeficiency virus type 1 nuclear import. J Virol 70(2), 1027-32 (1996).

Gallay, P., T. Hope, and D. Trono, HIV-1 infection of nondividing cells through the recognition of integrase by the importin/karyopherin pathway. Proc. Natl. Acad. Sci. USA 94(18), 9825 (1997).

Garrus, J. E., et al., Tsg101 and the vacuolar protein sorting pathway are essential for HIV-1 budding. Cell 107 (1), 55-65 (2001).

Gautier et al. Nucl. Acids Res. 15, 6625-6641 (1987).

Goff, S. P., Genetics of retroviral integration. Annu. Rev. Genet. 26:527-544 (1992).

Guyader, M., et al., Genome organization and transactivation of the human immunodeficiency virus type 2. Nature 326, 662-669 (1987).

Harris, D. and A. Engelman, Both the structure and DNA binding function of the barrier-to-autointegration factor contribute to reconstitution of HIV type 1 integration in vitro. J Biol Chem 275(50), 39671-7 (2000).

Haseloff and Gerlach Nature 334,585-591 (1988).

Hazuda, D. J., et al., Inhibitors of strand transfer that prevent integration and inhibit HIV-1 replication in cells. Science 287(5453), 646-50 (2000).

Helene Anticancer Drug Des. 6, 569-584 (1991).

Helene et al. Ann. N.Y. Acad. Sci. 660, 27-36 (1992).

Hindmarsh, P., et al., HMG protein family members stimulate human immunodeficiency virus type 1 and avian sarcoma virus concerted DNA integration in vitro. J Virol. 73(4), 2994-3003 (1999).

Inoue et al. Nucl. Acids Res. 15, 6131-6148 (1987a).

Inoue et al. FEBS Lett. 215, 327-330 (1987b).

Jarvis, R. A. & Ford, L. R. TechNotes 8(5) at www.ambion.com/techlib/tn/85/852.htm (2002).

Jenkins, T. M., et al., A soluble active mutant of HIV-1 integrase: involvement of both the core and carboxyl-terminal domains in multimerization. Journal of Biological Chemistry 271(13), 7712-8 (1996).

Kalpana, G. V. and S. P. Goff, Genetic analysis of homomeric interactions of human immunodeficiency virus type 1 integrase using the yeast two-hybrid system. Proc. Natl. Acad. Sci. USA 90, 10593-10597 (1993).

Kalpana, G. V., Marmon, S., Wang, W., Crabtree, G. R. & Goff, S. P. Binding and stimulation of HIV-1 integrase by a human homolog of yeast transcription factor SNF5 [see comments]. Science 266, 2002-6 (1994).

Kestler, H., et al., Induction of AIDS in Rhesus monkeys by molecularly cloned simian immunodeficiency virus. Science 248, 1109-1112 (1990).

Kingston, R. E. & Narlikar, G. J. ATP-dependent remodeling and acetylation as regulators of chromatin fluidity. Genes Dev. 13, 2339-52 (1999).

Krol et al. BioTechniques 6, 958-976 (1988).

Lai, L., et al., Moloney murine leukemia virus integrase protein augments viral DNA synthesis in infected cells. J Virol. 75(23), 11365-72 (2001).

Lama, J. and D. Trono, Human immunodeficiency virus type 1 matrix protein interacts with cellular protein H03. J Virol, 72(2), 1671-6 (1998).

Leavitt, A. D., Robles, G., Alesandro, N. & Varmus, H. E. Human Immunodeficiency Virus Type 1 Integrase Mutants Retain In Vitro Integrase Activity yet Fail to Integrase Viral DNA Efficiently during Infection. J. Virol. 70, 721-728 (1996).

Lee, M. S. and R. Craigie, Protection of retroviral DNA from autointegration: involvement of a cellular factor. Proc. Natl. Acad. Sci. USA 91(21), 9823-9827 (1994).

Lee, M. S. and R. Craigie, A previously unidentified host protein protects retroviral DNA from autointegration. Proc. Natl. Acad. Sci. USA 95(4), 1528-33 (1998).

Lee, D., et al., Interaction of El and hSNF5 proteins stimulates replication of human papillomavirus DNA. Nature, 1999. 399(6735): p. 487-91.

Lee, D., et al., SWI/SNF complex interacts with tumor suppressor p53 and is necessary for the activation of p53-mediated transcription. J Biol Chem 277, 22330-22337 (2002).

Lemaitre et al. Proc. Natl. Acad. Sci. U.S.A. 84,648-652 (1987).

Letsinger et al. Proc. Natl. Acad. Sci. U.S.A. 86, 6553-6556 (1989).

Leung, D. W., Chen, E. & Goeddel, D. V. A method for random mutagenesis of a defined DNA segment using a modified polymerase chain reaction. Techique 1, 11-15 (1989).

Liu, B., et al., Interaction of the human immunodeficiency virus type 1 nucleocapsid with actin. J Virol 73(4), 2901-8 (1999).

Lodi, P. J., et al., Solution structure of the DNA binding domain of HIV-1 integrase. Biochemistry 34, 9826-9833 (1995).

Maher Bioassays 14, 807-815 (1992).

Masuda, T., Planelles, V., Krogstad, P. & Chen, I. S. Y. Genetic Analysis of Human Immunodeficiency Virus Type 1 Integrase and the U3 att Site: Unusual Phenotype of Mutants in the Zinc Finger-Like Domain. J. Virol. 69, 6687-6696 (1995).

Mathe, C. & Nair, V. Potential inhibitors of HIV integrase. Nucleosides Nucleotides 18, 681-682 (1999).

Morozov, A., Yung, E. & Kalpana, G. Structure-function analysis of integrase interactor 1/hSNF5L1 reveals differential properties of two repeat motifs present in the highly conserved region. Proc. Natl. Acad. Sci. USA 95, 1120-1125 (1998).

Muchardt, C., Sardet, C., Bourachot, B., Onufryk, C. & Yaniv, M. A human protein with homology to *Saccharomyces cerevisiae* SNF5 interacts with the potential helicase hbrm. Nucleic Acids Res. 23, 1127-32 (1995).

Mulder, L. C. and M. A. Muesing, Degradation of HIV-1 integrase by the N-end rule pathway. J Biol Chem 275(38), 29749-53 (2000).

Mulder, L. C., L. A. Chakrabarti, and M. A. Muesing, Interaction of HIV-1 integrase with DNA repair protein hRad18. J Biol Chem 277(30), 27489-93 (2002).

Nair, V., HIV integrase as a target for antiviral chemotherapy. Rev Med Virol 12(3), 179-93 (2002).

Naldini, L. et al. In vivo gene delivery and stable transduction of nondividing cells by a lentiviral vector. Science 272, 263-267 (1996).

Nakamura, T. et al. Lack of infectivity of HIV-1 integrase zinc finger-like domain mutant with morphologically normal maturation. Biochem. Biophys. Res. Commun. 239, 715-722 (1997).

Ott, D. E. et al. Cytoskeletal proteins inside human immunodeficiency virus type 1 virions. J. Virol. 70, 7734-7743 (1996).

Ott, D. E., et al., Ubiquitin is covalently attached to the p6Gag proteins of human immunodeficiency virus type 1 and simian immunodeficiency virus and to the p12Gag protein of Moloney murine leukemia virus. J Virol 72(4), 2962-8 (1998).

Ott, D. E., et al., Actin-binding cellular proteins inside human immunodeficiency virus type 1. Virology 266(1), 42-51 (2000).

Pani, A. & Marongiu, M. E. Anti-HIV-1 integrase drugs: how far from the shelf? Curr. Pharm. Des. 6, 569-584 (2000).

Parissi, V., et al., Functional interactions of human immunodeficiency virus type 1 integrase with human and yeast HSP60. J Virol 75(23), 11344-53 (2001).

Patnaik, A., V. Chau, and J. W. Wills, Ubiquitin is part of the retrovirus budding machinery. Proc Natl Acad Sci USA 97(24), 13069-74 (2000).

Peytavi, R., et al., HEED, the product of the human homolog of the murine eed gene, binds to the matrix protein of HIV-1. J Biol Chem 274(3), 1635-45 (1999).

Phelan, M. L., et al., Reconstitution of a core chromatin remodeling complex from SWI/SNF subunits. Mol Cell 3(2), 247-53 (1999).

Pluymers, W., et al., Nuclear localization of human immunodeficiency virus type 1 integrase expressed as a fusion protein with green fluorescent protein. Virology 258(2), 327-32 (1999).

Pommier, Y. & Neamati, N. Inhibitors of human immunodeficiency virus integrase. Adv. Virus Res. 52, 427-458 (1999).

Priet, S., et al., Differential incorporation of uracil DNA glycosylase UNG2 into HIV-1, HIV-2, and SIV(MAC) viral particles. Virology 307(2), 283-9 (2003).

Radding, W., et al., Calmodulin and HIV type 1: interactions with Gag and Gag products. AIDS Res Hum Retroviruses 16(15), 1519-25 (2000).

Rosen, C. A., J. G. Sodroski, and W. A. Haseltine, Location of cis-acting regulatory sequences in the human T-cell leukemia virus type I long terminal repeat. Proc. Natl. Acad. Sci. USA 82, 6502-6506 (1985).

Rossi. Current Biology 4, 469-471 (1994).

Rozenblatt-Rosen, O., et al., The C-terminal SET domains of ALL-1 and TRITHORAX interact with the INI1 and SNR1 proteins, components of the SWI/SNF complex. Proc Natl Acad Sci USA 95(8), 4152-7 (1998).

Sarin et al. Proc. Natl. Acad. Sci. U.S.A. 85, 7448-7451 (1988).

Sayasith, K., G. Sauve, and J. Yelle, Targeting HIV-1 integrase. Expert Opin Ther Targets 5 (4), 443-464 (2001).

Sarver et al. Science 247, 1222-1225 (1990).

Stein et al. Nucl. Acids Res. 16, 3219 (1988).

Stevenson, M., Stanwick, T. L., Dempsey, M. P. & Lamonica, C. A. HIV-1 replication is controlled at the level of T cell activation and proviral integration. EMBO J. 9, 1551-1560 (1990).

Sussman, H. E. & Peirce, J. L. The Scientist 16, 44 at www.the-scientist.com/yr2002/jan/tools_020121.html (2002).

Swanstrom, R. & Wills, J. W. Synthesis, Assembly, and processing of Viral Proteins in Retroviruses (eds. Coffin, J. M., Hughes, S. H. & Vannus, H. E.) 263-334 (Cold Spring Harbor Laboratory Press, Cold Spring harbor, 1997).

Thali, M., et al., Functional association of cyclophilin A with HIV-1 virions. Nature 372(6504), 363-5 (1994).

VerPlank, L., et al., Tsg101, a homologue of ubiquitin-conjugating (E2) enzymes, binds the L domain in HIV type 1 Pr55 (Gag). Proc Natl Acad Sci USA 98(14), 7724-9 (2001).

Versteege, I. et al. Truncating mutations of hSNF5/INI1 in aggressive paediatric cancer. Nature 394, 203-6 (1998).

Wagner et al. Proc. Natl. Acad. Sci. U.S.A. 78,1441-1445 (1981).

Wai, J. S., et al., 4-Aryl-2,4-dioxobutanoic acid inhibitors of HIV-1 integrase and viral replication in cells. J Med Chem 43(26), 4923-6 (2000).

Wang, W. et al. Purification and biochemical heterogeneity of the mammalian SWI-SNF complex. Embo J. 15, 5370-82 (1996).

Wilk, T., B. Gowen, and S. D. Fuller, Actin associates with the nucleocapsid domain of the human immunodeficiency virus Gag polyprotein. J Virol 73(3), 1931-40 (1999).

Wilson, S. A., et al., Cloning and characterization of hIF2, a human homologue of bacterial translation initiation factor 2, and its interaction with HIV-1 matrix. Biochem J 342(1), 97-103 (1999).

Wiskerchen, M. & Muesing, M. A. Human immunodeficiency virus type 1 integrase: Effects of mutations on viral ability to integrate, direct viral gene expression from unintegrated viral DNA templates, and sustain viral propagation in primary cells. J. Virol. 69, 376-386 (1995).

Wu, X. et al. Functional RT and IN incorporated into HIV-1 particles independently of the Gag/Pol precursor protein. EMBO J. 16, 5113-22 (1997).

Wu, D. Y., et al., Epstein-Barr virus nuclear protein 2 (EBNA2) binds to a component of the human SNF-SWI complex, hSNF5/Ini1. J Virol 70(9), 6020-8 (1996).

Wu, X. et al. Human immunodeficiency Virus type 1 integrase protein promotes reverse transcription through specific interactions with the nucleoprotein reverse transcription complex. J. Virol. 73, 126-2135 (1999).

Yamamoto et al. Cell 22, 787-797 (1980).

Yung, E. et al. Inhibition of HIV-1 virion production by a transdominant mutant of integrase interactor 1. Nature Med. 7, 920-926 (2001).

Zaug et al. Science 224, 574-578 (1984).

Zaug and Cech Science 231, 470-475 (1986).

Zaug et al. Nature 324, 429-433 (1986).

Zon et al. Pharm. Res. 5, 539-549 (1988).

PCT Publication WO 88/09810.

PCT Publication WO 89/10134.

PCT Publication WO 90/11364.

PCT Publication WO 88/04300.

U.S. Pat. No. 5,093,246.

Although multi-drug therapy is an effective anti-HIV-1 treatment, viral relapses occur in at least half of the patients due to incomplete adherence to drug regimen, resulting in the emergence of drug resistant variants thus necessitating the development of new efficacious anti-HIV-1 therapeutic agents. HIV-1 proteins such as integrase (often abbreviated IN) and the cellular proteins implicated in viral replication are attractive new targets (Pani and Marongiu, 2000; Pommier and Neamanti, 1999; Mathe and Nair, 1999). Integrase catalyses integration of HIV-1 DNA into the host genome, an essential step in HIV-1 replication (Assante-Appiah and Skalka, 1997; Brown, 1990; Desrosiers, 1999). HIV-1 integrase consists of an N-terminal Zn-finger domain, a catalytic core domain with a conserved D, D (35) E motif, and a C-terminal domain. In vivo studies using molecular clones of HIV-1 have demonstrated that integrase mutations have pleiotropic effects, blocking other steps of viral replication in addition to integration (Assante-Appiah and Skalka, 1997; Brown, 1990; Desrosiers, 1999, Brown, 1997; Engleman et al., 1995; Masuda et al., 1995; Wu et al., 1999; Leavitt et al., 1996; Nakamura et al., 1997). Understanding the mechanism of these pleiotropic effects may lead to the development of antiviral drugs that affect multiple steps of HIV-1 life cycle, by simply targeting IN.

INI1/hSNF5, isolated via a yeast two-hybrid screen (Kalpana et al., 1994; Morozov et al., 1998), is the only known host protein that directly interacts with HUV-1 integrase (Leavitt et al., 1996; Nakamura et al., 1997). INI1/hSNF5 is a tumour suppressor and a core component of the SWI/SNF complex involved in chromatin remodelling (Versteege et al., 1998; Biegel et al., 1999; Wang et al., 1996; Kingston and Narlikar, 1999). It has three highly conserved domains, two of which are imperfect repeats (Rpt1 and Rpt2). HIV-1 integrase specifically binds to Rpt1 but not Rpt2 of INI1/hSNF5 despite their similarity (Morozov et al., 1998).

SUMMARY OF THE INVENTION

The present invention is based on the discovery that fragments of INI/hSNF5 that comprise the Rpt1 domain, aa 183-245, inhibit HIV-1 replication, particle production, and cell-to-cell spread. The HIV-1 inhibitory effect is more pronounced with shorter fragments, but longer fragments, including fragments aa 1-246 and 141-385, also inhibit HIV-1.

The invention is also based on the discovery that inhibiting production of INI1/hSNF5 by a cell inhibits HIV.

Accordingly, in some embodiments the present invention is directed to peptides comprising an Rpt1 domain of an INI1/hSNF5, which inhibit HIV-1 virion production in a human cell.

In other embodiments, the invention is directed to cells expressing the above peptides, vectors encoding the above peptides, and cells transfected with those vectors.

The present invention is also directed to methods of inhibiting replication or virion production of an HIV-1 in a mammalian cell, or spread of the HIV-1 to another cell. The methods comprise treating the cell with the above peptides.

Additionally, the invention is directed to related methods of inhibiting replication or virion production of HIV-1 in a mammalian cell, or spread of HIV-1 to another cell. The methods comprise treating the cell with the above-described vectors.

The invention is additionally directed to alternative methods of inhibiting replication or virion production of HIV-1 in a cell, or spread of the HIV-1 to another cell. The methods comprise inhibiting production of an INI1/hSNF5 by the cell.

The invention is also directed to methods of evaluating whether a test compound inhibits replication or virion production of HIV-1 in a cell, or cell-to-cell spread of HIV-1. The methods comprise determining whether the test compound inhibits the production of INI1/hSNF5 in the cell.

Additionally, the invention is directed to methods of evaluating whether a test compound inhibits replication or virion production of HIV-1 in a human cell, or cell-to-cell spread of HIV-1. The methods comprise determining whether the test compound disrupts the interaction of HIV-1 integrase with INI1/hSNF5.

In still other embodiments, the invention is directed to additional methods of inhibiting replication or virion production of an HIV-1 in a cell, or spread of the HIV-1 to another cell. The methods comprise treating the cell with a compound, where the HIV-1 inhibitory activity of the test compound was determined by the above-described evaluation methods. The invention is also directed to the test compounds themselves.

DETAILED DESCRIPTION OF THE INVENTION

Figure 1:
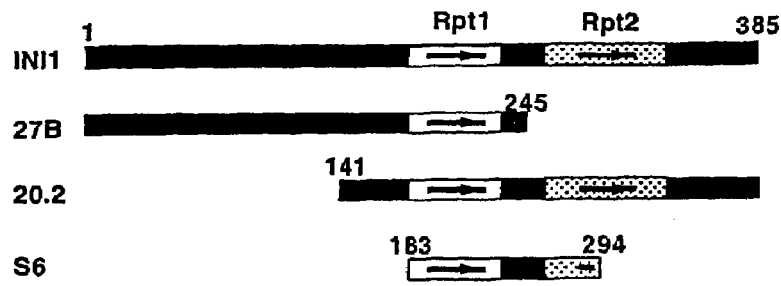
FIGS. 1A-1B provides graphs showing that a fragment of INI1/hSNF5, S6 (SEQ ID NO:3), inhibits HIV-1 particle production and replication. Panel 1A is a cartoon illustrating the INI1/hSNF5 fragments used. Names of the clones are indicated on the left side of each bar. The numbers above the bars represents amino acid residues of full length INI1/hSNF5 (SEQ ID NO:1) that the fragments encompass. Rpt1=repeat 1; Rpt2=repeat 2. Panel 1B is a logarithmic graph of intracellular and virion associated p24 antigen (pg/ml) in the presence and absence of INI1/S6 (average of three independent experiments). Viral vectors=open bars; Viral vectors+HA-INI1=hatched bars; Viral vectors+HA-S6=filled bars. Panel 1C shows the effect of S6 on the replication HIV-$1_{R3B}$ in Jurkat T-cells. The graph represents RT activity of the culture supernatants infected with HIV-$1_{R3B}$. Open triangle=Jurkat control; open square=pools of Jurkat T-cells stably expressing HA-INI1; filled circle=pools of Jurkat T-cells stably expressing HA-S6. Each data point represents RT activity of about 8 μl of culture supernatant.
Figure 1:
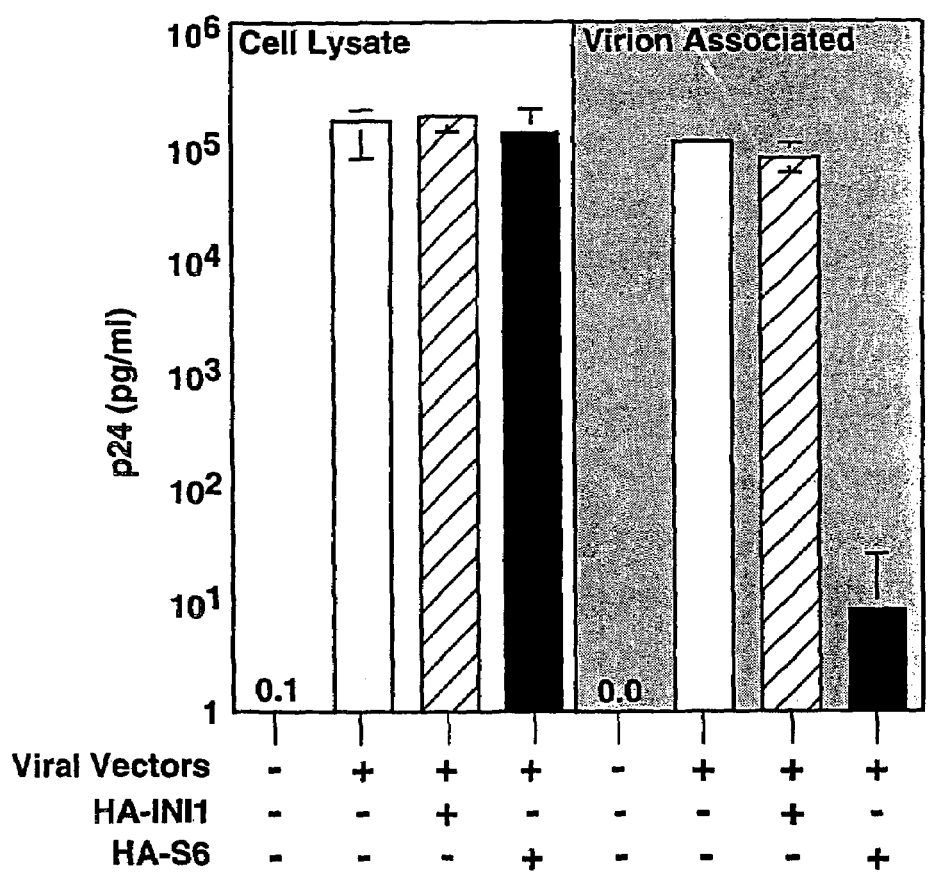

The present invention is based on the discovery, first described in Yung et al., 2001, that fragments of INI/hSNF5 that comprise the Rpt1 domain, exemplified herein as SEQ ID NO:2 (aa 183-245 of SEQ ID NO:1), inhibit HIV-1 replication, particle production, and cell to cell spread. The HIV-1 inhibitory effect is more pronounced with shorter fragments, such that the fragment consisting of aa 183-294, called the s6 fragment, completely inhibits HIV-1 particle production. However, longer fragments, including the fragment 1-245, have some inhibitory activity (see Example 1).

Without being bound by any particular mechanism, it is believed that the inhibitory fragments inhibit the interaction of INI1/hSNF5 by directly interacting with integrase within the context of Gag-Pol (see Example 1). Thus, the longer fragments are believed to inhibit HIV-1 production less than shorter fragments by providing partial INI1/hSNF5 functionality for HIV-1 replication. Since the Rpt1 domain interaction with HIV-1 integrase is the inhibitory aspect, it is expected that any peptide comprising an Rpt1 domain, other than a substantially complete INI1/hSNF5, would inhibit HIV-1 replication, particle production, and cell to cell spread.

Thus, in some embodiments, the invention is directed to peptides comprising an Rpt1 domain of an INI1/hSNF5, which inhibit HIV-1 virion production in a human cell.

Other than the Rpt1 domain, the peptide sequence is not narrowly limited and can include non-Rpt1 sequences, provided the non-Rpt1 sequences allow the Rpt1 domain to be available for interacting with HIV-1 integrase. The skilled artisan would be able to identify numerous peptides that would meet this criteria. Additionally, any peptide comprising an Rpt1 domain could be easily tested for anti-HIV-1 activity, e.g., by using the methods described in Example 1.

Thus, the non-Rpt1 regions can be another part of the INI1/hSNF5 protein, such that the peptide is a fragment of the INI1/hSNF5. The non-Rpt1 regions can also be a sequence not found in INI1/hSNF5, for example a functional protein, e.g., hemagglutinin (see Example 1). Additionally or alternately, the Rpt-1 containing peptide can be linked to a non-peptide molecule. Non-limiting examples include a nucleic acid molecule or a label such as a fluorescent molecule, a radioactive molecule, or a hapten or antigen that is subject to specific binding by a labeled antibody.

The portion of the peptide that is part of the INI1/hSNF5 protein preferably consists of amino acids 183-294 (SEQ ID NO:3) or a smaller portion which includes the entire Rpt1 domain (amino acids 183-245)(SEQ ID NO:2), however larger portions of the INI1/hSNF5 protein also are effective in inhibiting HIV-1 production. Nevertheless, as the size of the peptide that is homologous with INI1/hSNF5 increases in side, its ability to inhibit HIV-1 production decreases. For example, a peptide consisting of amino acids 141-395 of INI1/hSNF5 (SEQ ID NO:5) inhibits HIV-1 less effectively than the 183-294 peptide (SEQ ID NO:3), and a peptide consisting of amino acids 1-245 (SEQ ID NO:4) has less inhibitory than the 141-395 peptide (SEQ ID NO:5) (see Example 1).

The peptides of these embodiments prevent HIV-1 virion production in any cell capable of supporting HIV-1 replication. Preferred cells are those relevant to natural HIV-1 infection, i.e., human T cells, most preferably T-helper cells (CD4+).

In other embodiments, the present invention is directed to cells which comprise any of the above peptides that are capable of inhibiting HIV-1 virion production in a human cell. Preferably, the cells are mammalian cells, more preferably human cells, even more preferably human T cells. In most preferred embodiments, the cells are human T-helper cells. In other embodiments, the cell further comprises HIV-1. The peptide is preferably present in the cell in an amount sufficient to inhibit replication or virion production of HIV-1 in the cell, or spread of HIV-1 to another cell. Such cells will not support HIV-1 production. The peptide can be present due to treatment of the cell with the peptide. Alternatively, the peptide cen be present due to expression of the peptide (i.e., translation of genetic material present in the cell that encodes the peptide).

In additional embodiments, the invention is directed to vectors encoding peptides comprising an Rpt1 domain of an INI1/hSNF5, which inhibit HIV-1 virion production in a human cell. The peptides that can be encoded in the vectors are fully described above. In some aspects of these embodiments, the portion of the vector encoding the peptide comprises a fragment of the INI/hSNF5 gene, e.g., as provided herein as SEQ ID NO:6.

In preferred embodiments, the vector can be expressed in a mammalian cell that has been treated with the vector. Preferably, the cell is a human cell, most preferably a cell capable of being infected with HIV-1 (i.e., T-helper cells).

The vector of these embodiments are not narrowly limited to any particular form, and can be a viral vector, a plasmid vector, a cosmid vector, a linear naked DNA vector, or any other type of vector useful for any particular purpose. In aspects of the invention where the vector is used to transfect human cells to prevent HUV-1 production in those cells, preferred types of vectors are viral vectors and naked DNA vectors. In those aspects, the vector preferably causes the cell to express the truncated INI1/hSNF5 in amounts sufficient to inhibit replication or virion production of HIV-1 in the cell, or spread of HIV-1 to another cell.

Thus, in related embodiments, the invention is directed to cells transfected with the above vectors. These cells can be from any species, including bacteria or yeast (useful for storing and increasing the quantity of the vector by well-known methods) and mammalian cells (e.g., to prevent production of HIV-1 by the cell, were the cell to become infected with HIV-1). The cell can be in vitro or in vivo (e.g., a T cell in a human). Additionally, the cell can be removed from a human, transfected with the vector, then reintroduced into the human (ex vivo treatment). The cell can also further comprise HIV-1, wherein the transfection of the cell with the vector preferably causes the truncated INI1/hSNF5 to be expressed in amounts sufficient to inhibit replication or virion production of the HIV-1 in the cell, or spread of the HIV-1 to another cell.

The present invention is also directed to methods of inhibiting replication or virion production of an HIV-1 in a mammalian cell, or spread of the HIV-1 to another cell. The methods comprise treating the cell with any of the truncated INI1/hSNF5 peptides discussed above. Since peptides alone are generally unable to enter a cell, the peptides of these methods are preferably formulated in a composition that facilitates entry of the INI1/hSNF5 into the cell, such as a liposome composition, as are well-known in the art. In preferred embodiments the cell is a human cell, more preferably a human T cell, most preferably a human T-helper cell. The methods encompass in vitro, ex vivo, or in vivo treatments.

In similar embodiments, the invention is directed to other methods of inhibiting replication or virion production of an HIV-1 in a mammalian cell, or spread of the HIV-1 to another cell. These methods comprise treating the cell with any of the vectors previously discussed. Preferably, these methods also utilize human T-helper cells, and encompass in vitro, ex vivo, or in vivo treatments.

It has also been discovered that inhibiting the production of INI1/hSNF5 in the cell inhibits replication, virion production, and cell-to-cell spread of HIV-1 (see Example 1). This finding enables methods of inhibiting HIV-1 using specific inhibitory molecules such as ribozymes, antisense oligonucleotides, triplex-forming oligonucleotides and interfering RNAs, e.g. siRNAs. Techniques for the production and use of such molecules are well known to those of skill in the art.

Thus, in some embodiments, the present invention is directed to oligonucleotides comprising at least six nucleotides complementary to a contiguous sequence of a coding region of an INI1/hSNF5 gene. In these embodiments, the oligonucleotides inhibit expression of the INI1/hSNF5 gene in a cell.

An oligonucleotide sequence "complementary" to a portion of an RNA or DNA, as referred to herein, means a sequence having sufficient complementarity to be able to hybridize with the RNA or DNA, forming a stable duplex. The ability to hybridize depends on both the degree of complementarity and the length of the oligonucleotide. Generally, the longer the hybridizing oligonucleotide, the more base mismatches it may contain and still form a stable duplex (or triplex, as the case may be). One skilled in the art can ascertain a tolerable degree of mismatch by use of standard procedures to determine the melting point of the hybridized complex.

The oligonucleotides of the present invention should be at least six nucleotides in length, and are preferably ranging from 6 to about 50 nucleotides in length. In specific aspects, the oligonucleotide is at least 10 nucleotides, at least 15 nucleotides, at least 20 nucleotides or at least 50 nucleotides.

The oligonucleotides can also comprise a non-nucleotide moiety, such as a hapten, a fluorescent molecule, or a radioactive moiety, useful, e.g., to detect or quantify the amount of oligonucleotide that has entered the cell.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988), methylphosphonate oligonucleotides can be prepared by use of controlled pore glass polymer supports (Sarin, et al., 1988), etc.

The oligonucleotides can be DNA or RNA or chimeric mixtures or derivatives or modified versions thereof, single-stranded or double-stranded, depending on the purpose intended. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell markers in vivo, such as CD4, to improve the specificity of the oligonucleotide to cells likely to be infected with HUV-1), or agents facilitating transport across the cell membrane (see, e.g., Letsinger, et al., 1989; Lemaitre, et al., 1987; PCT Publication No. WO 88/09810) or the blood-brain barrier (see, e.g., PCT Publication No. WO 89/10134), hybridization-triggered cleavage agents (see, e.g., Krol et al., 1988) or intercalating agents (see, e.g., Zon, 1988). To this end, the oligonucleotide may be conjugated to another molecule, e.g., a peptide, hybridization triggered cross-linking agent, transport agent, hybridization-triggered cleavage agent, etc.

The oligonucleotide may comprise at least one modified base moiety including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl) uracil, and 2,6-diaminopurine.

The oligonucleotides may also comprise at least one modified sugar moiety including, but not limited to, arabinose, 2-fluoroarabinose, xylose, and hexose.

In other embodiments, the oligonucleotides comprise at least one modified phosphate backbone known in the art, for example a phosphorothioate, a phosphorodithioate, a phosphoramidothioate, a phosphoramidate, a phosphordiamidate, a methylphosphonate, an alkyl phosphotriester, a formacetal, or analog thereof.

In additional embodiments, the oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987). The oligonucleotide is a 2'-O-methylribonucleotide (Inoue, et al., 1987a), or a chimeric RNA-DNA analogue (Inoue, et al., 1987b).

In some aspects of these embodiments, the oligonucleotides of the present invention are antisense nucleic acids. Antisense nucleic acid molecules act to directly block the translation of mRNA by hybridizing to targeted mRNA and preventing protein translation. Antisense approaches involve the design of oligonucleotides which are complementary to a portion of an INI1/hSNF5 mRNA. The antisense oligonucleotides will bind to the complementary protective sequence mRNA transcripts and prevent translation. Absolute complementarity, although preferred, is not required.

Antisense molecules are preferably capable of being delivered to cells that are susceptible to HIV-1 infection. A number of methods have been developed for delivering antisense DNA or RNA to cells; e.g., antisense molecules can be injected directly into the tissue site, or modified antisense molecules, designed to target the desired cells (e.g., antisense linked to peptides or antibodies which specifically bind receptors or antigens expressed on the target cell surface) can be administered systemically.

A preferred approach to achieve intracellular concentrations of the antisense sufficient to suppress translation of endogenous INI1/hSNF5 mRNAs utilizes a recombinant DNA construct in which the antisense oligonucleotide is placed under the control of a strong promoter such as a pol III or pol II promoter. The use of such a construct to transfect target cells in a patient would be expected to result in the transcription of sufficient amounts of single stranded RNAs to form complementary base pairs with the endogenous INI1/hSNF5 transcripts and thereby prevent translation of the INI1/hSNF5 mRNA. For example, a vector can be introduced such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the INI1/hSNF5 antisense RNA can be by any promoter known in the art to act in mammalian, preferably human cells. Such promoters can be inducible or constitutive. Such promoters include but are not limited to: the SV40 early promoter region (Bemoist and Chambon, 1981), the promoter contained in the 3'-long terminal repeat of Rous sarcoma virus (Yamamoto, et al., 1980), the herpes thymidine kinase promoter (Wagner, et al., 1981), and the regulatory sequences of the metallothionein gene (Brinster, et al., 1982). Any type of suitable plasmid, cosmid, YAC or viral vector can be used to prepare the recombinant DNA construct that can be introduced directly into the tissue site. Alternatively, viral vectors can be used that selectively infect the desired tissue, in which case administration may be accomplished by another route (e.g., systemically).

Ribozyme molecules designed to catalytically cleave INI1/hSNF5 mRNA transcripts can also be used to prevent translation of INI1/hSNF5 mRNA and, therefore, expression of the INI1/hSNF5 protein. See, e.g., PCT Publication WO 90/11364; Sarver, et al., 1990.

Ribozymes are enzymatic RNA molecules capable of catalyzing the specific cleavage of RNA. For a review, see Rossi, 1994. The mechanism of ribozyme action involves sequence specific hybridization of the ribozyme molecule to complementary target RNA, followed by an endonucleolytic cleavage event. The composition of ribozyme molecules must include one or more sequences complementary to the INI1/hSNF5 mRNA, and must include the well known catalytic sequence responsible for mRNA cleavage. For this sequence, see, e.g., U.S. Pat. No. 5,093,246.

Figure 4:
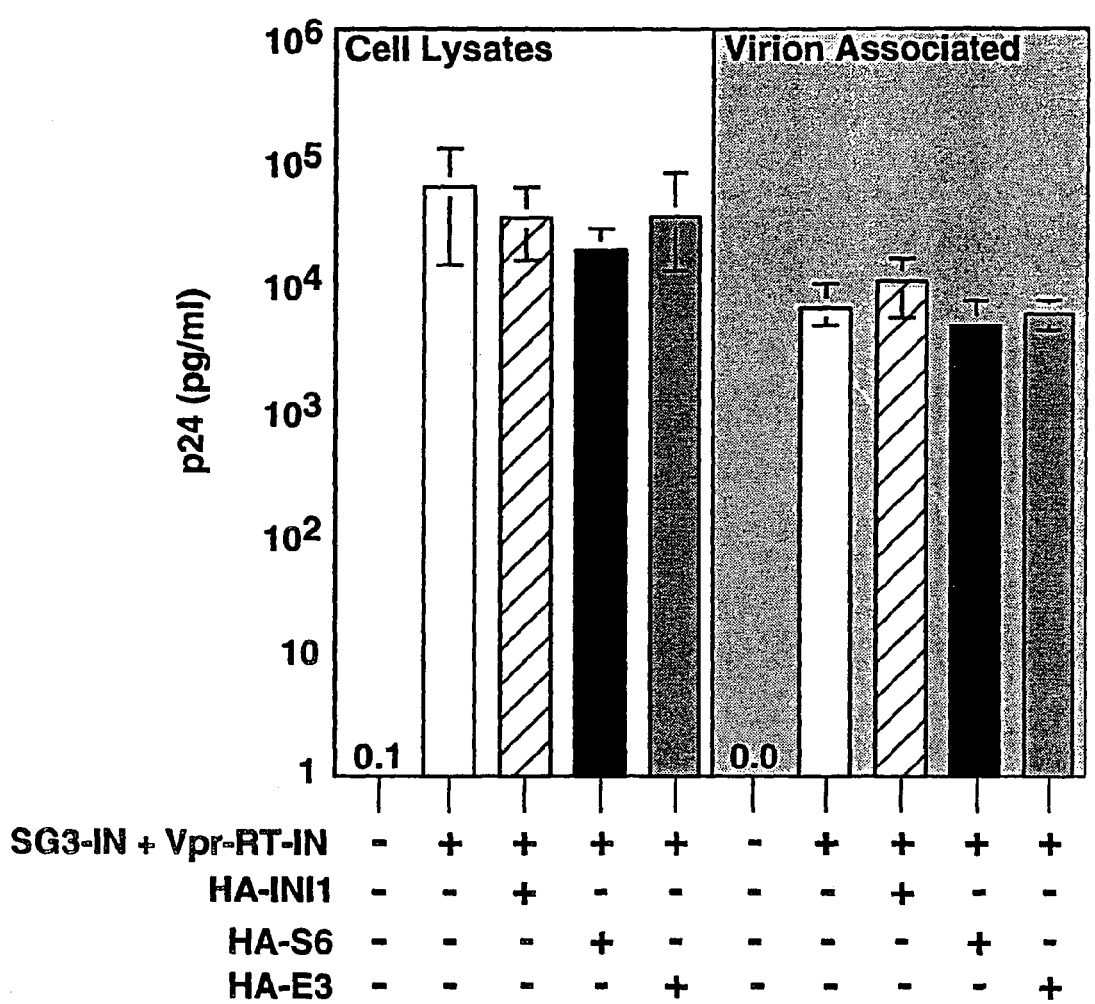
FIG. 4 depicts four micrographs showing the sub-cellular localization of INI1 and the truncation mutants S6 and E3. GFP, GFP-INI1, GFP-S6 or GFP-E3 represent the fusions proteins expressed in transfected 293T cells. The left panel in each row depicts the fluorescence due to GFP, the middle panel depicts the propidium iodide staining of the nuclei, and the right panel depicts the overlay of the two panels.

Preferred types of ribozymes for the present invention are hammerhead ribozymes. In these embodiments the hammerhead ribozymes cleave INI1/hSNF5 mRNA at locations dictated by flanking regions which form complementary base pairs with the mRNA. The sole requirement of the hammerhead ribozyme is that the mRNA have the two base sequence 5'-UG-3', which occurs numerous times in the INI1/hSNF5 gene (see SEQ ID NO:6). The construction and production of hammerhead ribozymes is well known in the art and is described more fully in Myers, 1995, Molecular Biology and Biotechnology: A Comprehensive Desk Reference, VCH Publishers, New York, (see especially FIG. 4, page 833) and in Haseloff and Gerlach, 1988.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Been and Cech, 1986; Zaug, et al., 1984; Zaug and Cech, 1986; Zaug, et al., 1986; WO 88/04300, Cell, 47:207-216). The Cech-type ribozymes have an eight base pair active site that hybridizes to the INI1/hSNF5 mRNA sequence wherever cleavage of the INI1/hSNF5 RNA is desired. The invention encompasses those Cech-type ribozymes that target eight base-pair sequences that are present in the INI1/hSNF5 gene.

As with the antisense approach, the ribozymes can be composed of modified oligonucleotides (e.g., for improved stability, targeting, etc.) and should be delivered to cells that are susceptible to HIV infection in vivo, preferably T-helper cells. A preferred method of delivery involves using a DNA construct "encoding" the ribozyme under the control of a strong constitutive pol III or pol II promoter, so that transfected cells will produce sufficient quantities of the ribozyme to destroy endogenous INI1/hSNF5 gene messages and inhibit translation. Because ribozymes, unlike antisense molecules, are catalytic, a lower intracellular concentration is required for efficiency.

Alternatively, endogenous target gene expression can be reduced by targeting deoxyribonucleotide sequences complementary to the regulatory region of the INI1/hSNF5 gene (i.e., the INI1/hSNF5 gene promoter and/or enhancers) to form triple helical structures which prevent transcription of the INI1/hSNF5 gene in target cells in the body. See generally, Helene, 1991; Helene, et al., 1992; Maher, 1992.

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizable stretches of either purines or pyrimidines to be present on one strand of a duplex. Nucleic acids may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen which are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex. Several such GC-rich areas are available for targeting in the INI1/hSNF5 gene (SEQ ID NO:6).

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In other embodiments, the oligonucleotide can be a small interfering RNA (siRNA), known in the art to be double stranded RNAs, complementary to the target mRNA (here INI1/hSNF5), that interacts with cellular factors to bind to the target sequence, which is then degraded. The siRNA sequence can be complementary to any portion of the INI1/SNF5. The siRNA is preferably 21-23 nt long, although longer sequences will be processed to that length. References include Caplen et al., 2001; Elbashir et al., 2001; Jarvis and Ford, 2002; and Sussman and Peirce, 2002.

Antisense RNA and DNA, ribozyme, triple helix, and siRNA molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid-phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. In another alternative, antisense cDNA constructs that synthesize antisense RNA constitutively or inducibly, depending on the promoter used, can be introduced stably into cell lines.

In related embodiments, the present invention is directed to additional methods of inhibiting replication or virion production of HIV-1 in a mammalian cell, or spread of the HIV-1 to another cell. These methods comprise inhibiting production of an INI1/hSNF5 by the cell. Preferably, production of the INI1/hSNF5 is inhibited with any of the above-described antisense, ribozyme, triple helix, and/or siRNA oligonucleotides described above.

For these embodiments, the cell is also preferably a human cell that can support HIV-1 infection and/or multiplication, such as a T-helper cell. In some embodiments, the cell is treated in vitro, then preferably implanted into a human at risk for HIV-1 infection. In other embodiments, the cell is treated in vivo.

The present invention is also directed to methods of evaluating whether a test compound inhibits replication or virion production of HIV-1 in mammalian cells, or cell-to-cell spread of HIV-1. The methods comprise determining whether the test compound inhibits the production of INI1/hSNF5 in the cell. The compound can be a nonoligonucleotide compound such as a nonpeptide molecule, or a peptide. However, in preferred embodiments, the test compound is an oligonucleotide, preferably complementary to a contiguous sequence of a coding region of an INI1/hSNF5 gene. Non-limiting examples of such oligonucleotides are oligonucleotides designed to be antisense RNA and DNA, ribozymes, triple helix, or siRNAs.

In some preferred embodiments, the determination of the ability of the test compound to inhibit production of INI1/hSNF5 is made by measuring INI1/hSNF5 protein production by the cell after treatment of the cell with the compound. In other preferred embodiments, the determination is made by measuring INI1/hSNF5 mRNA production by the cell after treatment of the cell with the compound. Preferably, the cell is a human cell that can support HIV-1 infection and/or multiplication, such as T helper cells.

Other embodiments of the present invention include additional methods of evaluating whether a test compound inhibits replication or virion production of HIV-1 in a human cell, or cell-to-cell spread of HIV-1. The methods comprise determining whether the test compound disrupts the interaction of HIV-1 integrase with INI1/hSNF5. The disruption can be determined using a fragment of the INI1/hSNF5 that also interacts, such as a peptide comprising an Rpt1 domain, as previously described. The INI1/hSNF5 or fragment, or integrase used in these methods can also comprise a non-peptide component, for example a label (e.g., a radioactive or flourescent label, or a hapten or antigen that allows binding of a labeled antibody).

Methods of inhibiting replication or virion production of the HIV-1 in a mammalian cell, or spread of the HIV-1 to another cell, by treating the cell with a test compound, where the HIV-1 inhibitory activity of the test compound was determined by the above-described methods, are also envisioned as within the scope of the invention, as are the test compounds themselves.

Preferred embodiments of the invention are described in the following Examples. Other embodiments within the scope of the claims herein will be apparent to one skilled in the art from consideration of the specification or practice of the invention as disclosed herein. It is intended that the specification, together with the Examples, be considered exemplary only, with the scope and spirit of the invention being indicated by the claims which follow the Examples.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1989); "Current Protocols in Molecular Biology" Volumes I-IV, Ausubel, R. M., ed. (1997); Myers, "Molecular Biology and Biotechnology: A Comprehensive Desk Reference" (1995) and "Cell Biology: A Laboratory Handbook" Volumes I-III, J. E. Celis, ed. (1994).

EXAMPLE 1

INI1/SNF5 Fragments Inhibit HIV-1 Production

Since HIV-1 integrase (IN) has pleiotropic effects, we sought to identify fragments of INI1/hSNF5 that bind to IN and interfere with any of the steps in HIV-1 replication. We report here that expression of a minimal IN-binding fragment of INI1/hSNF5 (S6) drastically inhibits HIV-1 assembly, particle production and replication in a transdominant manner. Genetic and biochemical analyses indicate that this effect is due to direct interaction of S6 with IN within the context of Gag-Pol in vivo. Furthermore, INI1/hSNF5 is incorporated into the virions and is necessary for efficient particle production. These observations indicate that INI1/hSNF is important for HIV-1 replication and provide novel strategies for developing antiviral agents.

Methods

Construction and expression of INI1 truncations in mammalian cells. The generation of INI1 deletions in pGADNot have been previously described (Nakamura et al., 1997). BamHI-BglII fragment containing INI1/hSNF5 cDNA were isolated from clones 27B (aa. 1-245) (SEQ ID NO:4), 20.2 (aa. 141-385)(SEQ ID NO:5) and S6 (aa. 183-294)(SEQ ID NO:3) and inserted into the BamH1 site of pCGN, to generate clones expressing various haemagglutinin (HA) fusions. Plasmid pGFP-INI1 expressing GFP fused to the N-terminus of INI1/hSNF5 (SEQ ID NO:1), was generated by inserting a 1.3 kb EcoRI fragment of pSH2-INI1 into the EcoRI site of pEGFP-C2 (Clontech, Palo Alto, Calif.). Plasmid pGFP-S6 and pGFP-E3 were generated by PCR using pGADNot-S6 and pGADNot-E3, respectively, as a template, and by using primers EC2 (5'-CCGCTCTAGAT-CAACCGAGGGC-3') (SEQ ID NO:7) and EC7 (5'-CGAATTCCGGATGCGCGAGCCC-3') (SEQ ID NO:8), and inserting the digested fragment at XbaI and EcoRI sites of pEGFP-C2.

Transfection, Viral particle production and p24 assays. 293T cells at 30% confluency were transfected with a 2:1:1 ratio (20 µg) of transducing vector (pHR'CMV-GFP or pHR'CMV-LacZ), pMDG (expressing the VSVG envelope protein), and pCMVDR8.2 (expressing Gag-Pol) along with 20 µg of either pCGN-INI1, pCGN-S6, or pCGN-S6 mutants, using the calcium phosphate transfection method (Cat# S-001, Specialty Media Inc., Phillipsburg, N.J.) as per the manufacturer's instructions. In MON cells, a total of 10 µg of three plasmid-based vectors was used. The effect of INI1, S6 or E3 on the production of replication-competent molecular clone HIV-$1_{R3B}$, or three plasmid based vectors carrying the H12Y mutation in IN, or SG3-IN virus carrying Vpr-RT-IN, was also determined by co-transfecting the respective viral constructs with pCGN-INI1, pCGN-S6 or pCGN-E3 plasmids using the calcium phosphate method as above. The p24 ELISA assays were carried out using the NEN kit (Cat # NEK-050A).

Intracellular levels of p24 antigen in transfected cells were determined by lysing the cells from a 10 cm plate in 0.2 ml of RIPA buffer. The supernatant was filtered through a 0.2 mM acetate filter (Costar, Cambridge, Mass., Cat# 8112) before use in p24 ELISA or in immunoblot analyses.

Generation of pools of Jurkat stable cell lines expressing HA-INI1 or HA-S6. Approximately $5 \times 10^6$ Jurkat cells were electroporated at 250V and 1.07 µF, and plated out in 5 ml of RPMI media (Gibco, Carlsbad, Calif.) in 60 mm dishes. About 24 hr post-electroporation, 1.25 mg/ml G-418 was added and selected for 18 days until all the untransfected cells were eliminated. Pools of resistant cells expressing either HA-INI1 or HA-S6 were amplified and were used as target cells for infection with HIV-$1_{R3B}$. The expression of HA-INI1 and HA-S6 in these cells were verified by immunoblot analysis using α-HA antibodies (data not shown).

Reverse two-hybrid analysis. A library of S6 mutants was generated by taking advantage of the low fidelity of Taq polymerase in the presence of manganese. PCR was carried out using pGADNot-S6 as the template, 5'Gal and 3'Gal oligonucleotides as primers, and Taq polymerase (NEB, Beverly, Mass.) with an annealing temperature of 50° C. The PCR fragments were then digested with BamH1 and Sal1 and cloned into pGADNot to generate a library of S6 mutants as fusions to GAL4-AC (activation domain). This library was screened against the bait plasmid, LexA-DB (DNA binding) fusion of HIV-1 integrase in yeast, and non-interacting mutants of S6 were isolated as those resulting in white colonies upon X-Gal staining. Plasmids were rescued from the yeast colonies, re-tested and sequenced to determine the mutations. Four clones that contained single point mutations were sub-cloned into a pCGN vector to express HA-fusion proteins in mammalian cells.

Co-immunoprecipitation studies. 293T cells were transiently transfected with 20 μg of either pCGN, pCGN-INI1 or pCGN-S6 along with SG3-IN and Vpr-RT-IN using the calcium phosphate method. Forty eight hours post-transfection, the cells were harvested and lysed in Buffer L (Stevenson, 1990) and pre-cleared with Protein A Sepharose, then incubated with polyclonal antibody against HA (Santa Cruz Biotech, Santa Cruz, Calif. Cat#SC-805). Protein-antibody complexes were subsequently incubated with Protein A-Sepharose. Bound proteins were washed in Buffer L containing 125 mM NaCl, separated by SDS/PAGE and analyzed by immunoblot analysis using anti-integrase or anti-INI1 antibodies, and chemiluminescent detection.

Preparation of H12Y virions. A BclI-ClaI fragment of pCMVDR8.2 was subcloned into pBluescript to generate an intermediate vector. The H12Y substitution was introduced into the intermediate vector using the Quickchange method (Stratagene, La Jolla, Calif.), and the entire region was sequenced to confirm the presence of the H12Y mutation and the absence of any other mutations. The BclI-ClaI fragment containing the H12Y mutation was subsequently cloned into the pCMVΔR8.2 vector, to generate pCMV-H12Y. This clone was transfected into 293T cells along with pHR'CMV-LacZ and pMDG for generating pseudotyped H12Y virions.

Sub-cellular localization of GFP-INI1/S6/E3. 293T cells were cultured and transfected, using a standard calcium phosphate method, on 12 mm circular cover-slips (0.13-0.17 mm in thickness) that had been autoclaved. 24 hr post-transfection, cells were fixed with 2% paraformaldehyde, washed and permeabilized in 1% Triton X-100, and then treated with 1 μg/ml RNase A before staining with propidium iodide (40 μg/ml). Cells were mounted on a glass slide and confocal images were captured on a BioRad MRC6000 machine (Richmond, Calif.).

Results

Inhibition of HIV-1 particle production and replication by a fragment of INI1/hSNF5. We generated a panel of INI1/hSNF5 truncations containing the minimal integrase-interaction domain, Rpt1, as HA fusions (FIG. 1A), confirmed their expression upon transient transfection into 293T cells, and first tested their effect on post-integration events of HIV-1 replication leading to assembly and budding. We co-expressed HA-tagged INI1 fragments along with a three-plasmid-based HIV-1 vector system (Naldini et al., 1996) in 293T cells and monitored the particle production by p24 ELISA of the culture supernatants. Our results indicate that while full length INI1/hSNF5 had no significant effect, different truncation mutants affected particle production to varying degrees (Table 1). We focussed our attention on one truncation mutant, S6 (aa 183-294 of INI1/hSNF5—SEQ ID NO:3), for further analysis, since it reduced viral production to undetectable levels (Table 1). Furthermore, HA-S6 but not full length HA-INI1/hSNF5 potently inhibited particle production of HIV-1$_{R3B}$, a replication-competent molecular clone, in transfected 293T cells (Table 2).

TABLE 1

Inhibition of HIV-1 virion production by INI1 truncations.

| Plasmids | Protein expression[a] | P24 of culture supernatants (ng/ml) | % inhibition[b] |
|---|---|---|---|
| Mock | N/A | 0.00 | N/A |
| Viral vectors[c] | N/A | 113.28 | 0% |
| Viral vectors + pCGN-INI1 | ++ | 115.05 | 0% |
| Viral vectors + pCGN-27B (HA-ΔINI1 aa 1-245) | ++ | 95.57 | 16% |
| Viral vectors + pCGN-20.2 (HA-ΔINI1 aa 141-385) | ++ | 35.37 | 69% |
| Viral vectors + pCGN-S6 (HA-ΔINI1 aa 183-294) | +++ | 0.00 | 100% |

[a]Expression of INI1 and its truncations were determined by immunoblot analysis using α-HA antibodies.
[b]Amount of p24 produced with viral vectors alone was considered to be 100%. The inhibition is expressed as 0% for this sample. The % inhibition in p24 levels in other samples was calculated relative to that of viral vectors alone.
[c]Viral vectors are pCMVΔR8.2, pMDG and pHR'-CMV-LacZ.

TABLE 2

Inhibition of R3B virion production by S6.

| Plasmids | p24 of culture supernatants (ng/ml) | % inhibition[a] |
|---|---|---|
| Mock | 0 | N/A |
| R3B | >264.09 | 0% |
| R3B + pCGN-INI1 | >264.09 | 0% |
| R3B + pCGN-S6 (HA-ΔINI1 aa183-294) | 0.69 | >99.74% |

[a]Amount of p24 produced with R3B alone was considered to be 100%. The inhibition is expressed as 0% for this sample. The % inhibition in p24 levels in other samples was calculated relative to that of R3B alone.

To rule out the possibility that the decrease in viral particle production is due to the effect of HA-S6 on the intracellular viral protein synthesis, we examined the levels of both the intracellular and virion-associated p24. Multiple experiments confirmed that 293T cells co-transfected with S6 contained similar intra-cellular p24 levels compared to that of cells co-transfected with INI1 (FIG. 1B). Nevertheless, p24 levels in the culture supernatants from cells co-transfected with S6 were drastically reduced and consistently yielded 10,000 to 100,000 times less p24 antigen than the controls (FIG. 1B). These results indicate that the inhibition of particle production by HA-S6 was not due to a decrease in the intracellular levels of viral proteins.

To determine if inhibition of late events by HA-S6 is sufficient to abrogate the spread of the replication-competent HIV-1 through the natural target cells, we generated a pool of Jurkat T-cell clones stably expressing HA-S6, and infected them with either 0.3 or 1.67 m.o.i. (multiplicity of infection) of HIV-1$_{R3B}$. We monitored the viral spread by assaying reverse transcriptase activity in culture supernatants (FIG. 1C). The results indicate that while the control Jurkat cells supported infection by HIV-1$_{R3B}$ that reached a peak production at day 10, the pool of Jurkat cell clones expressing HA-S6 showed significantly decreased levels of viral replication even after two weeks of culture. Residual replication of HIV-1$_{R3B}$ seen in the pool of cells expressing HA-S6 is likely due to the presence of cells expressing low or no HA-S6. These results strongly suggest that the dominant-negative mutant is effective in protecting T-cells from infection by HIV-1.

IN-interaction-defective mutations in S6 abrogate the inhibitory effect. To determine if inhibition of particle production by HA-S6 is due to its specific interaction with IN, we isolated IN-interaction-defective mutants of S6. We generated a library of S6 mutants using PCR-based random mutagenesis (Leung et al., 1989). A reverse yeast two-hybrid system was then employed to screen this library for mutants of S6 that do not interact with a LexA DNA-binding domain fusion of IN (pSH2-IN) (Morozov et al., 1998). Of the several IN-interaction-defective mutants obtained, four contained single amino acid substitutions (E3, E4, E7, E10, and FIG. 2A). All four mutations were located within the C-terminal half of the Rpt1 portion of S6, which is encoded by a single exon, suggesting that these mutations are present within one functional domain (FIG. 2A).

To test if the IN-interaction-deficient variant of S6 would result in a reduced inhibition of particle production, three-plasmid-based HIV-1 vectors were co-transfected into 293T cells with full-length INI1, HA-S6 or HA-S6 mutants and both intra-cellular and particle associated p24 were measured. There was no significant difference in intracellular p24 levels between the cells co-transfected with HA-S6 or IN-interaction-defective HA-S6 mutants. As before, HA-S6 severely reduced the levels of extracellular p24. However, each of the four mutants resulted in significantly lower inhibition of p24 production compared to that of HA-S6 (FIG. 2B). The strongest reversal of inhibition (a 2-fold inhibition as opposed to 80,000-fold with HA-S6) was obtained with the HA-E3 mutant carrying a glycine substitution at the invariant D224 residue (FIG. 2B). We determined the number of infectious units per ml in culture supernatants produced in 293T cells expressing HA-INI1, HA-S6 or HA-E3 by using CMV-LacZ markers (Ott et al., 1996). The results indicated that while expression of HA-S6 resulted in a background level of infectivity, expression of HA-E3 resulted in only about 2-fold decrease in the viral titers as compared to that of the control (FIG. 2C). These results suggest that the loss of inhibition is correlated with the increased production of infectious virus particles.

Figure 2:
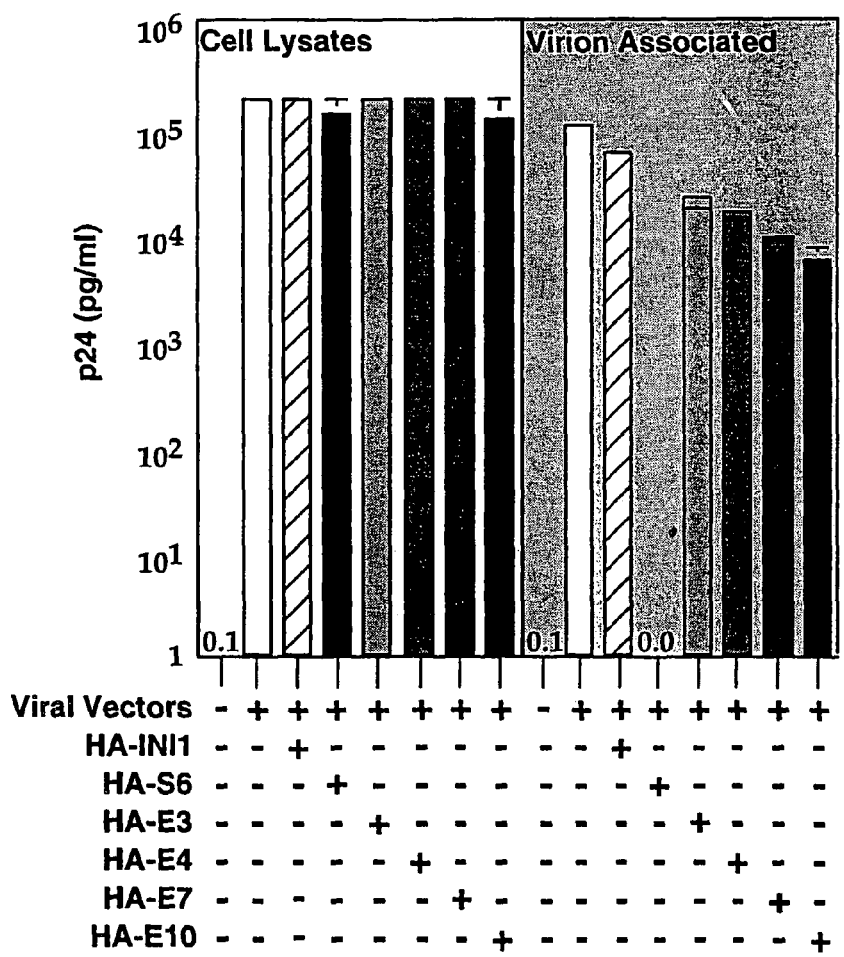
FIGS. 2A-2D provides graphs and photographs showing that interaction defective mutants of S6 abrogate the inhibitory effect on viral particle production. Panel 2A shows the location of substitution mutations found in the integrase-interaction defective mutants of S6, isolated by using a reverse two-hybrid system. The mutants are E3 (SEQ ID NO:9), E4 (SEQ ID NO:10), E7 (SEQ ID NO:11), and E10 (SEQ ID NO:12). The highly conserved residues of INI1/hSNF5 are indicated in bold. Repeat 1 and Repeat 2 represents the two highly conserved domains of INI1/hSNF5. The regions of S6 encoded by specific exons are indicated at the bottom. Substitutions in S6 mutants, E3-E10 are indicated. Panel 2B is a logarithmic graph showing that integrase-interaction defective mutants of S6 abrogate the inhibition of particle production by S6. The graph plots intracellular ("Cell Lysates") and virion associated p24 antigen (pg/ml) in the presence and absence of INI1, S6, E3, E4, E7 and E10 (average of three independent experiments). From left to right are no virus; viral vectors only (open bar); viral vectors+HA-INI1 (hatched bar); viral vectors+HA-S6 (black bar); viral vectors+HA-E3 (lightest shading); viral vectors+HA-E4 (darker shading); viral vectors+HA-E7 (darker shading); viral vectors+HA-E10 (darkest shading). Panel 2C is a graph showing the infectivity of the virus produced in the presence and absence of HA-INI1, or HA-S6, or HA-E3. Infectious units refers to the number of LacZ positive cells obtained after staining with X-gal, when infected with culture supernatants carrying pseudotyped HIV-1-lacZ virus. Panel 2D are photographs of the results of immunoblot analysis to determine the relative amounts of INI1, S6, E3, E4, E7, E10 and Gag-Pro-Pol in the producer cells. The upper panel is an immunoblot probed with anti-integrase antibody; the lower panel is an immunoblot probed with α-HA antibody. 2E, Co-immunoprecipitation analysis to determine the association of HA-INI1, HA-S6, and HA-E3 with Vpr-RT-IN in vivo. Plasmids that are transfected into 293T cells are indicated above each lane. The immunoprecipitations were performed using α-HA antibody and immunoblotted with a monoclonal α-IN antibody (top panel) to determine the co-immunoprecipitation of Vpr-RT-IN, or with an α-HA antibody (bottom panel) to determine the levels of INI1/S6/E3 in the immunoprecipitates.
Figure 2:
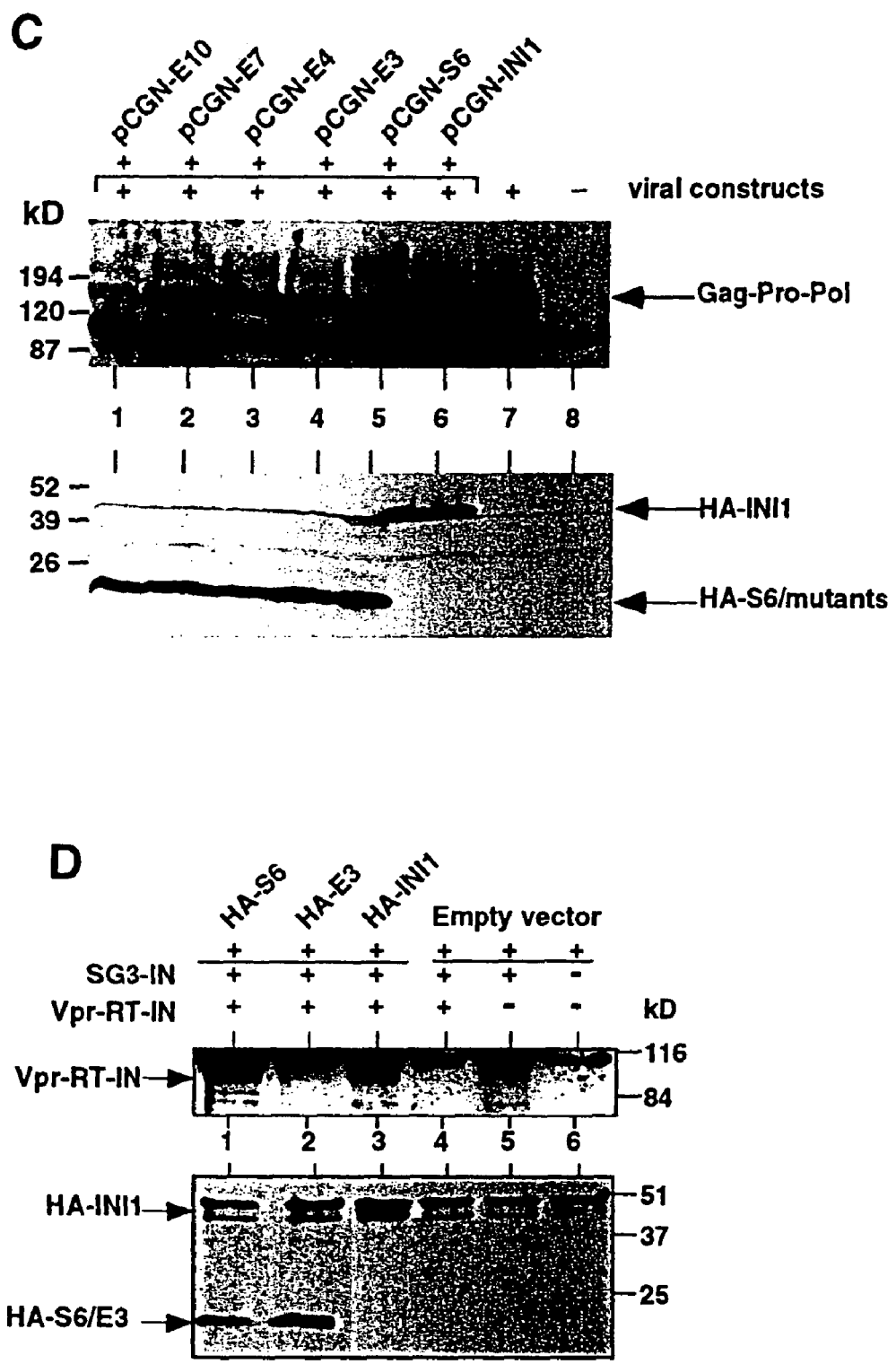

Immunoblot analysis of lysates from cells co-transfected with HA-S6 or its mutants, along with HIV-1 based vectors, indicated that S6 and all four point mutants were expressed at equivalent levels (FIG. 2D, bottom). In addition, immunoblot analysis of the same lysates using α-IN antibody to determine the levels of Gag-Pol indicated no significant increase of this polyprotein in cells transfected with E3, E4, E7 or E10 as compared to that with S6 (FIG. 2D, top). This result suggested that reversal of inhibition is not due to an increase in Gag-Pol protein in the presence of S6 mutants.

To confirm that the S6 mutants do not interact with IN expressed as part of Pol in vivo, we co-transfected 293T cells with plasmids expressing HA-INI1, HA-S6 or HA-E3 along with Vpr-RT-IN (Wu et al., 1997). In addition, we co-transfected SG3-IN, a molecular clone of HIV-1 carrying a premature stop codon at the end of RT, to assess any potential effect of other viral proteins such as Gag or Env on this interaction. Immunoprecipitation was carried out using the α-HA antibody. The precipitated proteins were probed with α-IN and α-HA antibodies. Our results indicated that while both HA-INI1 and HA-S6 were able to co-immunoprecipitate Vpr-RT-IN, the S6 mutant HA-E3, although present at similar or higher levels in the lysate, was not (FIG. 2E). This experiment indicates for the first time that INI1/hSNF5 and S6 can interact with IN in vivo and confirms our finding that E3 is a true interaction-defective mutant of S6.

Figure 3:
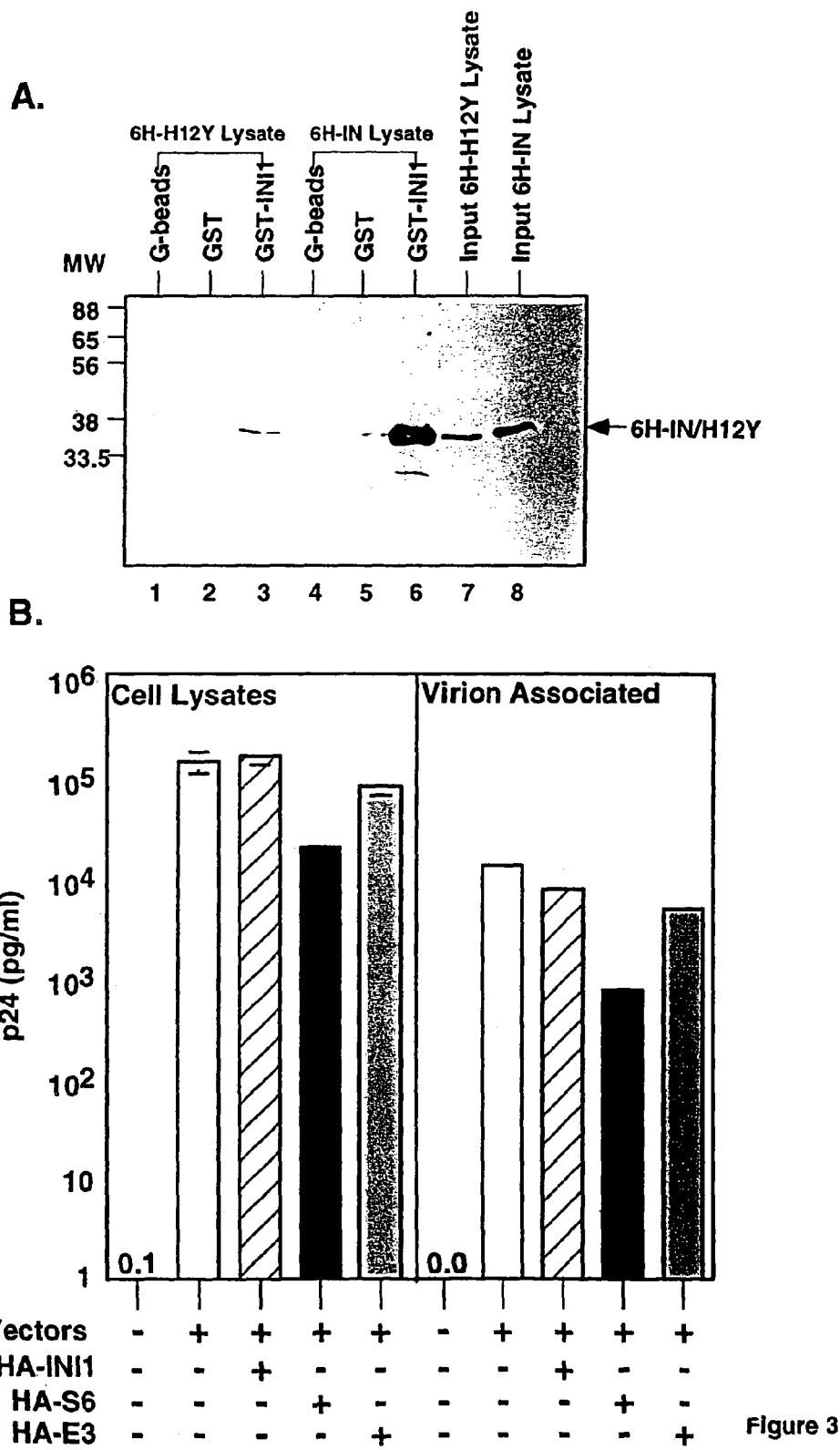
FIGS. 3A-3B summarizes results from experiments establishing that INI1-interaction defective mutation in integrase abrogates the inhibitory effect of S6. Panel 3A is a photograph of an immunoblot resulting from in vitro binding studies of GST-INI1/hSNF5 with 6H-IN and 6H-H12Y. The panel illustrates the immunoblot analysis of the proteins bound to GST proteins, using a-6H antibodies. G-beads=glutathione agarose beads. Lanes 1-3 represent the binding of GST-INI1/hSNF5 to 6H-H12Y and lanes 4-6 represent binding of GST-INI1/hSNF5 protein to 6H-IN. Panel 3B is a graph summarizing results from experiments showing that H12Y mutation abrogates the inhibitory effect of S6. The panel is a logarithmic graph of intracellular and virion associated p24 antigen (pg/ml) of H12Y virus in the presence and absence of INI1/S6/E3 (average of three independent experiments). Panels 3C and 3D are graphs summarizing results from experiments showing that S6 does not affect the virus production of an integrase deficient HIV-1. Panel 3C shows that HIV-1 virus (SG3-IN) containing Vpr-RT-IN was produced in the presence and absence of HA-INI1, HA-S6 or HA-E3. The panel is a logarithmic graph of intracellular and virion associated p24 antigen (pg/ml) of SG3-IN+Vpr-RT-IN in the presence and absence of INI1/S6/E3 (average of three independent experiments). Panel 3D is a graph that represents a number of lacZ positive cells obtained after infecting P4 (HeLa/CD4+/LTR-LacZ) cells with 1 ml of culture supernatants containing SG3-IN+Vpr-RT-IN virus produced in the presence and absence of HA-INI1, HA-S6 and HA-E3.

INI1/hSNF5-interaction-defective IN mutation abrogates S6-mediated inhibition. The loss of inhibition by the IN-interaction-defective mutants of S6 indicated that the IN-S6 interaction is necessary for the inhibitory effect. Similarly, viruses carrying INI1-interaction-defective mutations in IN may not be inhibited by S6. To test this, we isolated an INI1 interaction-defective mutant of IN using a reverse yeast two-hybrid screen. One of the clones recovered had a point mutation that resulted in substitution of the histidine at $12^{th}$ position to tyrosine (H12Y). We carried out an in vitro GST-pull down assay to confirm that the H12Y IN mutant is defective for interaction with INI1/hSNF5 (FIG. 3A). Consistent with the yeast two-hybrid analysis, we found that the H12Y mutant had greatly reduced binding to INI1/hSNF5 in vitro than that of the wild-type IN, despite comparable levels of input proteins (FIG. 3A, compare lanes 3 and 6). These results confirm that the mutation in the Zn-finger domain disrupts the IN-INI1 interaction.

We incorporated the H12Y mutation into the pCMVΔR8.2 plasmid that encodes the Gag-Pol polyprotein of the three-plasmid-based HIV-1 vector. The effect of HA-INI1, HA-S6 or HA-E3 on the H12Y mutant virus production in 293T cells was tested as before by co-transfections. The intracellular p24 levels of H12Y virus were similar to that of the wild-type virus (Compare FIGS. 1B and 3B). There was a uniform 10-fold decrease in the extracellular particle-associated p24 levels of H12Y virus compared to that of the corresponding intracellular p24 levels (FIG. 3B). These results indicate that the H12Y mutation by itself decreases the particle production 10-fold. Repeated experiments indicated that co-transfection of HA-S6 resulted in approximately 10-fold decrease in the level of H12Y virion associated p24 production as opposed to a 10,000 to 100,000-fold decrease in p24 production noticed with that of wild type (FIG. 3B). This 10-fold decrease in virion-associated p24 of H12Y virus may be due to a corresponding reduction in the intracellular p24 levels in the presence of HA-S6 (FIG. 3B). Thus, the above results indicate that introduction of an INI1-interaction defective mutation into IN significantly abrogates the inhibitory effect of S6.

S6-mediated inhibition requires the presence of IN within Gag-Pol. It has been reported that certain IN substitution mutations affect HIV-1 particle production probably due to their effect on the processing of Gag-Pol (Adachi et al., 1991; Ansari-Lari et al., 1995; Cannon et al., 1994; Gallay et al., 1995; Stevenson et al., 1990; Wiskerchen and Muesing, 1995). These effects could be overcome if IN is removed from Gag-Pol and IN mutants are provided in trans as Vpr or Vpr-RT fusions (Wu et al., 1997; Fletcher, 1997). We surmised that binding of S6 to IN might mimic the effects of these IN mutations. Therefore, we tested the effect of S6 on particle production of the SG3-IN virus that carries a stop codon at the end of RT, and trans-complemented IN as a Vpr-RT-IN fusion. The results indicated that there was no significant difference in the intracellular p24 levels, and with IN no longer being a part of Gag-Pol, there was no significant difference in the extracellular p24 levels with or without S6 (FIG. 3C). Furthermore, no significant differences were noticed in the infectivity of the culture supernatants in the presence and absence of HA-S6 when assayed using P4 (HeLa CD4$^+$/LTR-LacZ) cells (Wu et al., 1997) (FIG. 3D). These results strongly suggest that inhibition by S6 requires IN to be part of Gag-Pol.

While INI1/hSNF5 is nuclear, S6 is predominantly cytoplasmic. The above results indicate that S6 inhibits viral particle production by directly interacting with IN, and by interfering with some steps of the assembly or budding process that involves Gag-Pol. However, INI1/hSNF5 is a nuclear protein (Muchardt et al., 1995), and these late events occur in the cytoplasm. To reconcile this paradox, we hypothesised that S6 might be localized in the cytoplasm and that the dominant-negative effects of S6 may be due to its ectopic expression. To test this hypothesis, we expressed INI1, S6 and the interaction-defective mutant E3 as GFP-fusion proteins in 293T cells and observed their sub-cellular localization by confocal microscopy. The results indicate that while INI1 is nuclear, S6 is predominantly cytoplasmic (FIG. 4), confirming our hypothesis. Interestingly, the IN-interaction-defective S6 mutant E3 also exhibited cytoplasmic localization (FIG. 4), indicating that mere cytoplasmic localization is not sufficient for transdominant inhibition and that interaction with IN is required.

Figure 5:
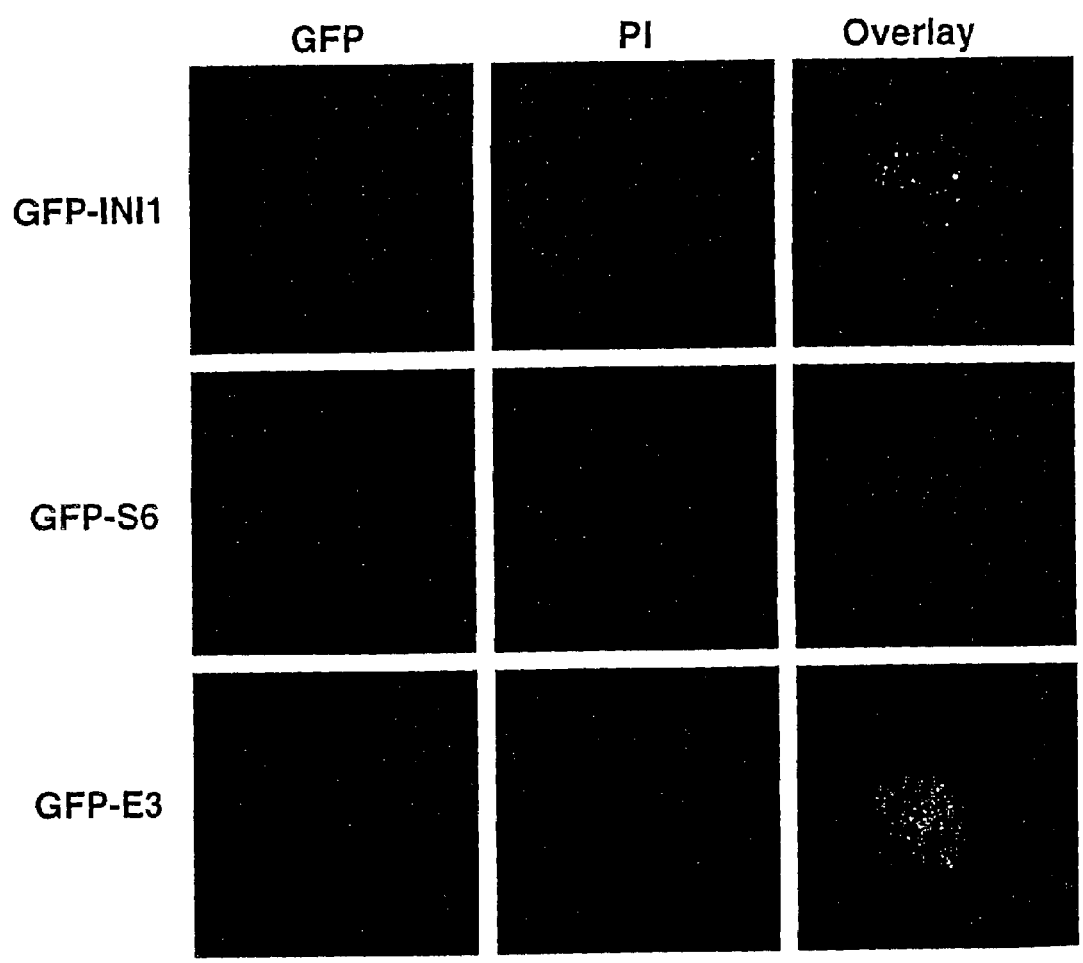
FIG. 5 depicts results from experiments establishing that INI1/hSNF5 is required for efficient particle production and is encapsulated in the virions. Panel 5A is a graph showing the particle production and infectivity of HIV-1 produced in INI1$^{-/-}$ MON cells. Plasmids transfected into MON cells and the amounts are indicated below the graph. The values are expressed as fold increase as compared to that of the control MON cells transfected with empty vector (expressed as 1). Filled bars are virion-associated p24 (pg/ml); open bars are infectious units/ml determined using GFP marker; Shaded bare is intracellular p24 (pg/ml). Panel 5B depicts a sequential immunoblot analysis of purified HIV-1$_{MN}$ virions treated with subtilisn and probed with α-INI1, α-gp41, or α-gp24 antibodies (Ab). Panel 5C depicts immunoblots showing the incorporation of tagged HA-INI1 into HIV-1$_{R3B}$. Immunoblots show an analysis of subtilisn treated HIV-1$_{R3B}$ virus produced from 293T cells in the presence and absence of HA-INI1.

INI1/hSNF5 is required for efficient HIV-1 particle production. The interference of late events by S6 implies that INI1/hSNF5 may be important for these stages of HIV-1 replication. To determine if INI1/hSNF5 is indeed required for HIV-1 late events, we tested a MON cell line that carries a homozygous deletion of the INI1 gene (Adachi et al., 1991) for its ability to support HIV-1 particle production. We found that when three-plasmid-based vectors were introduced into MON cells, both p24 production and infectivity were significantly reduced (about 10-100 fold decrease as compared to that of 293T cells). To determine if the decrease is due to the lack of INI1/hSNF5, we co-transfected MON cells with increasing concentrations of INI1/hSNF5 along with constant amounts of viral vectors. Our results indicate that while co-expression of INI1/hSNF5 only slightly increased the p24 levels within MON cells, it significantly rescued the defect in viral particle production in a dose-dependent manner (FIG. 5A). This increase in p24 production was correlated with a corresponding increase in the number of infectious particles in the culture supernatants (FIG. 5A), suggesting that INI1/hSNF5 is required for the efficient production of infectious virions.

INI1/hSNF5 is incorporated into HIV-1 virions. Interestingly, pseudotyped HIV-1 particles, produced from the 293T cells, were able to efficiently infect MON cells, suggesting that these INI1$^{-/-}$ cells support early events in HIV-1 replication. One possible explanation for this result is that INI1/hSNF5, present in 293T cells, is packaged into the virions and is sufficient for carrying out early events in INI1$^{-/-}$ MON cells. To test this hypothesis, we purified and concentrated HIV-1$_{MN}$ virions by sucrose density gradient sedimentation and subjected them to subtilisn treatment (Ott et al., 1996). The total proteins from this treatment were subjected to successive rounds of immunoblot analysis with α-INI1, α-gp41 (SU) and α-p24 antibodies (FIG. 5B). The results indicate that similar amounts of INI1/hSNF5 are present in both untreated and subtilisn treated virions. Use of α-gp41 revealed that subtilisn treatment was complete in these samples. To further confirm this observation, we examined the ability of tagged INI1/hSNF5 to get incorporated into HIV-1$_{R3B}$ virions. The virus particles, produced from the 293T cells in the presence or absence of transiently transfected HA-INI1/hSNF5, were subjected to the subtilisn treatment and immunoblot analysis as above (FIG. 5C). The results indicate that HA-INI1/hSNF5 is specifically incorporated into virions. These data for the first time indicate that HIV-1 virions encapsidate INI1/hSNF5.

Discussion

We have demonstrated a novel method of inhibiting HIV-1 replication using a 111aa fragment of INI1/hSNF5. This fragment strongly inhibited HIV-1 particle production in a dominant-negative manner, reducing the p24 amount by more than 10,000-fold. S6 also inhibited the spread of replication-competent HIV-1 in T-cell cultures. Our results indicate that this inhibition is mediated by a direct interaction of S6 with IN within the context of Gag-Pol. First, IN-interaction-defective mutants of S6 that we isolated do not display drastic inhibition of particle production. Second, viruses carrying an INI1-interaction-defective mutant of IN (H12Y) are not significantly inhibited by S6. And third, removal of IN from Gag-Pol resulted in the abrogation of this inhibition. Furthermore, we found that unlike the nuclear INI1/hSNF5, S6 predominantly localizes to the cytoplasm, suggesting that its ectopic expression is responsible for the inhibitory effect. To our knowledge, this is the first example of a truncation fragment of a cellular protein inhibiting late events of HIV-1 replication via IN.

It has been previously reported that although Pol or IN is not necessary for the assembly and budding of HIV-1, mutations in IN have severe effects on these processes (Engleman et al., 1995; Leavitt et al., 1996; Wiskerchen and Muesing, 1995; Bukovsky and Gottlinger, 1996). The binding of S6 with the IN portion of Gag-Pol may mimic the effects of such IN mutations and therefore could similarly block some steps of late events. We propose that when S6 binds to IN, it may interfere with the proper multimerization of Gag and Gag-Pol by steric hindrance, affect maturation, block an interaction of the cellular assembly machinery with Gag-Pol, or mediate the mis-localization of viral proteins into a different sub-cytoplasmic compartment. Removing IN from Gag-Pol and providing it in trans as a Vpr-fusion overcomes these defects, as S6 can no longer physically interact with Gag-Pol deleted of IN. Interestingly, packaging of Vpr into mature virions may involve mechanisms distinct from that for Gag-Pol and hence Vpr-RT-IN incorporation is not inhibited by S6.

Our results indicate that INI1/hSNF5 is important for HIV-1 replication. In addition to the dominant-negative effect of the INI1/hSNF5 mutant, our results show, for the first time that INI1/hSNF5 is packaged in the virions. Furthermore, we have found that there is a reduction in particle production in cell lines homozygously deleted for the INI1 gene, and that INI1/hSNF5 expression corrects this defect in a dose dependent manner. The observed 10-fold decrease in particle production of INI1-interaction defective mutant H12Y suggests that the IN-INI1 interaction plays a role in these processes. Our attempts to study the effect of S6 on early events resulted in no significant inhibition (data not shown), which is likely due to the cytoplasmic localization of S6. However, this data does not preclude the possibility that full-length INI1/hSNF5 influences early events in viral replication.

The identification of a small fragment of a cellular protein that acts as a potent dominant-negative inhibitor especially of the late events of HIV-1 life cycle provides exciting possibilities for therapeutic intervention of AIDS. S6 does not appear to be cytotoxic, as cells stably expressing S6 grow normally (data not shown). Since S6 is a fragment of a host protein, it is unlikely to be immunogenic. In addition, mutations that make IN defective for interaction with INI1 or S6 may also render the virus replication defective, thus making it harder to develop resistance to S6. Gene therapy to deliver S6 or its derivatives to hematopoietic stem cells could be a useful strategy to control HIV-1 infection. Furthermore, the profound inhibition of late events by S6 makes it an attractive candidate for developing effective small molecular weight drugs for controlling re-emergence of HIV-1 from latently infected cells.

EXAMPLE 2

Specificity of Interaction of INI1/hSNF5 with Retroviral Integrases and its Functional Significance

EXAMPLE SUMMARY

Integrase interactor 1 (INI1)/hSNF5, is a host factor that directly interacts with HIV-1 IN and is incorporated into HIV-1 virions. We have found that while INI1/hSNF5 is completely absent from purified microvescicular fractions, it is specifically incorporated into virions with a IN:INI1/hSNF5 stoichiometry of approximately 2:1 molar ratio. In addition, we have found that INI1/hSNF5 is not incorporated into related primate lentiviral and murine retroviral particles despite the abundance of the protein in producer cells. This specificity in incorporation appears to be correlated with the ability of INI1/hSNF5 to exclusively interact with HIV-1 integrase but not with other retroviral integrases. Additional evidence of specificity comes from the observations that the inhibition of particle production by the transdominant mutant S6, harboring the minimal IN-interaction domain of INI1/hSNF5, is restricted to HIV-1 and that the particle production by other retroviruses is unaffected by this mutant in 293T cells. Taken together, these results suggest that INI1/hNSF5 is a specific host factor for HIV-1 and that S6 is a potent inhibitor of viral replication that is highly specific to HIV-1.

Introduction

Despite effectiveness of HAART therapy in controlling the Human Immunodeficiency Virus type 1 (HIV-1) replication, emergence of drug resistant viruses in infected patients and the severe side effects caused by the currently used drugs necessitates the continued search for new and improved therapeutic strategies for controlling AIDS. HIV-1 encoded proteins such as integrase (IN) and the cellular proteins that are implicated in HIV-1 life cycle are attractive targets for development of antivirals.

IN catalyzes the integration of viral cDNA into the host genomic DNA, a process that is essential for the replication of all retroviruses and is the step that results in the latently infected form of the virus. During the life cycle of a retrovirus, IN is produced as part of Gag-Pol polyprotein, assembled into virions and subsequently cleaved into individual components during maturation (Brown, 1997). IN consists of three distinct structural domains, the N-terminal zinc-binding domain (HHCC), the central core domain with highly conserved D,D(35)E motif forming the catalytic residues and the less highly conserved C-terminal domain. Although crystal structure data exists for single and double domains of IN, no structural data exists yet for the entire IN protein (Esposito and Craigie, 1999). IN has been shown to multimerize by using various biochemical and genetic approaches (Andrake and Skalka, 1995; Engelman et al., 1993; Kalpana and Goff, 1993) but the exact nature and order of the IN multimer is still unknown (Jenkins et al., 1996; Cherepanov et al., 2003).

Studies of IN have demonstrated that it may have effects on steps in viral replication besides integration itself. For example, IN mutations R199C, R199A and W235E mutations have been shown to affect viral morphology, decreased particle formation and infectivity (Wiskerchen and Muesing, 1995; Leavitt et al., 1996). Mutations in the Zn-finger region of IN (H12A) or deletions have been shown to decrease particle production, cause defects before or at the initiation of reverse transcription and decreases in particle associated RT activity (Wu et al., 1999; Lai et al., 2001). IN has also been implicated to be required for the nuclear localization of the pre-integration complex (PIC) and although controversial, several putative NLS in its protein sequence have been implicated in this process (Gallay et al., 1997; Pluymers et al., 1999; Bouyac-Bertola et al., 2001; Dvorin et al., 2002).

Taken together, these studies indicate that mutations of IN are pleiotropic and may alter viral replication by blocking various steps other than integration itself. Although the mechanistic basis for the pleiotropic effects of IN mutants is unclear, these results suggest that strategies that target IN could affect multiple steps besides integration.

In Example 1, we have demonstrated that the Rpt1region of INI1/hSNF5 is necessary and sufficient to bind to HIV-1 IN. Subsequent studies from ours and other laboratories demonstrated that INI1/hSNF5 interacts with various viral and cellular proteins such as EBNA2 (Wu et al., 1996), c-MYC (Cheng et al., 1999), ALL1 (Rozenblatt-Rosen et al., 1998), HPV18-E1 (Lee et al., 1999) and p53 (Lee et al., 2002), and that many of these interactions involve the Rpt regions of INI1/hSNF5, indicating that these domains include protein-protein interaction domains. Furthermore, studies from our laboratory indicated that INI1/hSNF5 has a masked nuclear export sequence (NES) located at the beginning of Rpt2 (Craig et al., 2002) and a non-specific DNA binding activity upstream of Rpt1 (Morozov et al., 1998). INI1/hSNF5 is a homologue of yeast transcription factor SNF5, and is a component of the ATP dependent chromatin remodeling mammalian SWI/SNF complex (Wang et al., 1996). Reconstitution of SWI/SNF activity from purified proteins revealed that INI1/hSNF5, BAF170, BAF155 and the ATPase subunit, BRG1 or hBRM, form the critical core components of the complex (Phelan et al., 1999). Recent studies have suggested that INI1/hSNF5 is also a tumor suppressor mutated in a typical teratoid and malignant rhabdoid tumors (AT/RT), or malignant rhabdoid tumors (MRT) an aggressive pediatric tumor with poor prognosis (Versteege et al., 1998), which results in a 100% mortality rate in early childhood.

Targeting interaction between IN and the host cellular factors may prove to be a fruitful area of investigation for development of antivirals against HIV-1. In an attempt to develop IN inhibitors using cellular proteins, we previously isolated and characterized a transdominant mutant of INI1/hSNF5 (Example 1). We demonstrated that a fragment of INI1/hSNF5 (S6) spanning the minimal IN-interaction domain profoundly inhibited the HIV-1 particle production (10,000 to 100,000 fold). Stable expression of S6 resulted in protection of the T-cells from infection by full-length clones of HIV-1. Mutations in S6 or IN that disrupt IN-INI1 interaction abrogated the inhibitory effect, suggesting that S6 inhibits particle production by directly binding to IN. An IN-deficient HIV-1 containing Vpr-RT-IN in trans was not affected by S6 suggesting that IN within the context of Gag-Pol is required for this inhibition. In addition, we found that the truncation fragment S6 is ectopically expressed in the cytoplasm, while INI1 is nuclear. Taken together, our studies suggest that ectopic over-expression of a minimal IN-binding domain of INI1 transdominantly inhibits HIV-1 particle production and replication. Furthermore, by analyzing the purified and subtilisn treated virions, we found that INI1/hSNF5 is incorporated into the HIV-1 particles.

Gene therapy strategies to deliver the transdominant mutant, S6, into hematopoietic stem cells could be a useful approach to protect T-cells from infection. However, since the transdominant mutant inhibits HIV-1 assembly and particle production, it precludes the use of lentiviruses as delivery system for this purpose. Furthermore, it is not clear if the transdominant mutant affects assembly and particle production of other retroviruses and whether or not INI1/hSNF5 interacts with other retroviral integrases. Therefore, in this report we have examined: (i) the specificity of interaction of INI1/hSNF5 with retroviral integrases; (ii) the ability of INI1/hSNF5 to be incorporated into various primate lentiviral and murine retroviral particles; and (iii) the effect of the transdominant mutant on particle production of these other retroviruses. We found that INI1/hSNF5 is specifically incorporated into HIV-1 but not the other retroviral particles tested. This HIV-1 specific incorporation was correlated with the ability of INI1/hSNF5 to interact with HIV-1 but not the other retroviral integrases. In addition, INI1/hSNF5 transdominant mutant S6 inhibited particle production of HIV-1 but not that of the other retroviruses. Taken together, these results demonstrate a specific incorporation of INI1/hSNF5 into HIV-1 virions and a potent and specific inhibitory effect of S6 on HIV-1 viral replication.

Materials and Methods

Yeast two-hybrid. DNA fragments encoding the IN open reading frames of HIV-2ROD10, SIVmac239 (Kestler et al., 1990; Guyader et al., 1987), and HTLV-1 (Rosen et al., 1985), were cloned into yeast vectors as fusions to both LexA DNA binding domain (LexADB) and GAL4 activation domain (GAL4AD). The DNA fragments were PCR-amplified using Vent polymerase and primer pairs: i) GKSIV-A (CGCGGATCCTCTTCTTGGAAAAGATA-GAGCCA) (SEQ ID NO:13) and GKSIV-C (CGGAATTC-CTATGCCACCTCTCTAGA) (SEQ ID NO:14) for SIV IN, ii) GKHIV2-A (CGCGGATCCTGTTCCTG-GAAAAAATAGAG) (SEQ ID NO:15) and GKHIV2-C (CGGAATTCTATGCCATTTCTCCATCC) (SEQ ID NO:16) for HIV-2 IN, and iii) HTLV-1F (CGGAATTCGTC-CTGCAGCTC) (SEQ ID NO:17) and HTLV-1R (GCGAAT-TCTTACCCATGGTG) (SEQ ID NO:18) for HTLV-1 IN.

The amplified HIV-2 IN (IN-2) and SIV IN (IN-S) fragments were digested with BamH1 and EcoRI and were first cloned into pGEX3xPL to generate GST-fusions. The amplified HTLV IN (IN-T) fragment was digested with EcoRI and cloned into the EcoRI site of pGEX1T. The gene fusions were sequenced to ensure the absence of PCR mediated errors. The BamHI and EcoRI fragments of IN-2 and IN-S were then excised from the recombinants and ligated with EcoRI-SalI adapters. These fragments were cloned into the BamHI and SalI sites of pSH2-1 (encoding LexADB), and pGADNot (encoding GAL4AC). The two EcoR I ends of the HTLV-1 IN (IN-T) fragment was modified to BamHI by the addition of EcoRI-XmnI-BamHI adapters, and cloned into the BamHI site of pSH2-1 and pGADNot.

In vitro binding. A BamH1/SalI fragment of INI1 WAS isolated from pSP72-INI1 and cloned into pQE32 vector (Qiagen) to generate a fragment of INI1 as a fusion to hexa-histidine (6His). The stable expression of recombinant proteins in bacteria was confirmed using both anti-INI1 antibodies (INI1-PB3) and anti-6H antibodies (Clontech). The various GST-IN proteins were induced and then were immobilized onto G-beads Morozov et al., 1998). The GST-IN-S was expressed at low levels. To carry out the in vitro binding reaction, the GST and GST-IN proteins that were immobilized onto G-beads were incubated with 200 µl of crude bacterial lysates containing either 6H-INI1 or 6H-IN-1 proteins in HND buffer (20 mM HEPES, pH 7.0, 200 mM NaCl, 4 mM $MgCl_2$, 5 mM DTT, 0.1% IGEPAL, 100 mg/ml BSA, 2 µg/ml aprotinin, 2 µg/ml leupeptin, 2 µg/ml pepstatin A, 18 µg/ml PMSF) as described before (Morozov et al., 1998). The bound proteins were washed, separated by SDS-PAGE, immunoblotted and detected by a chemiluminescence detection method using anti-6H antibodies (Clontech, cat# 8904-1).

Transfections. 293T cells were co-transfected with 20 g of pCGN the INI1 transdominant mutant, S6, (Example 1) along with 5 µg of the full-length molecular clones of HIV-1R3B, HIV-2, MuLV, SIVmac (AIDS repository cat #133) and HTLV-1 (AIDS repository cat# 2817) using a calcium phosphate transfection method (Specialty Media S-001) per manufacturer's recommendations.

Reverse tranacriptase (RT) assay. The effect of the S6 transdominant mutant was monitored by carrying out reverse transcriptase (RT) assays of culture supernatants as follows. One ml of culture supernatants from cells transfected with HIV-1R3B, HIV-2, SIVmac, HTLV-1 and MuLV were precipitated by adding 0.5 ml of 30% PEG-8000/0.4M NaCl overnight at 4° C. The precipitated sample was centrifuged at 8000×g for 45 minutes at 4° C. The precipitate was resuspended in solution B (0.9% Triton X-100, 440 mM KCl) and 4 volumes of solution A was added (25 mM Tris pH 7.8, 0.25 mM EDTA, 0.025% Triton-X100, 50% glycerol, 10 mM DTT and 100 mM KCl). Five µl of this virion sample was incubated with an RT reaction cocktail for 1 hr at 37° C. The reaction cocktails for all viruses except MuLV consisted of 50 mM Tris pH 8.0, 20 mM DTT, 60 mM NaCl, 5 µM oligo dT, 10 µM poly rA, 10 µM dTTP, 10 µCi of $\alpha$-$^{32}$P-dTTP, 10 mM $MgCl_2$, 0.0005% NP-40. The reaction cocktail for MuLV consisted of 60 mM Tris pH 8.3, 24 mM DTT, 0.7 mM $MnCl_2$, 75 mM NaCl, 6 µM oligo dT, 12 µM poly rA, 10 µCi of $\alpha$-$^{32}$P-dTTP 12 µM dTTP, 0.0006% NP-40. The reactions were carried out at 37° C. for 60 minutes. After the incubation, 10 µL of each reaction were spotted onto DE82 paper (Whatman), washed 3 times in 2×SSC buffer with gentle agitation, rinsed in 100% ethanol and dried under infrared light. The DE82 squares containing the RT reaction spots were then cut out, placed into scintillation fluid and counted in a scintillation counter.

Virion preparation. Culture supernatant was harvested and passed through a low-protein binding syringe filter (Fisher cat #:09-740-37F) to remove cellular particulates. This virus was concentrated by sucrose density centrifugation and then subtilisn-digested as previously documented (Ott et al., 1996). Briefly, the concentrated virus was resuspended in 1×PBS and treated with 1 mg/ml subtilisn and digested overnight (~18 hours) at 37° C. After digestion, PMSF was added to a final concentration of 5 µg/ml to inactivate the subtilisn. The digested virus was centrifuged over 10 ml of a 20% sucrose solution with 5 g/ml PMSF. The 10 ml of 20% sucrose solution was carefully layered to form a "pad" under the virus sample and the remaining space in the centrifuge tube was filled with 1×PBS containing 5 µg/ml PMSF. After centrifugation in an SW28Ti rotor at 25,000 rpm for 3 h, the PBS and the top ~⅓ volume of the sucrose was carefully removed. The remaining trace of sucrose solution was carefully removed using a fresh pipette tip. The pellet was then gently washed in 1×PBS to remove the remaining sucrose. The resulting concentrated subtilisin-treated virions were resuspended in 2× lysis buffer (0.125 M Tris pH 6.8, 4% SDS, 20% glycerol, 1.8% β-mercaptoethanol, 0.0025% bromophenol blue). The virion proteins were separated on SDS-PAGE and subjected to immunoblot analysis using anti-INI1 antibodies (PB3), anti-p24 antibodies to detect the levels of HIV-1 capsid, anti-p30 antibodies to detect MuLV capsid and anti-gp41 antibodies to confirm the complete subtilisn digestion in virion samples.

Results

Figure 6:
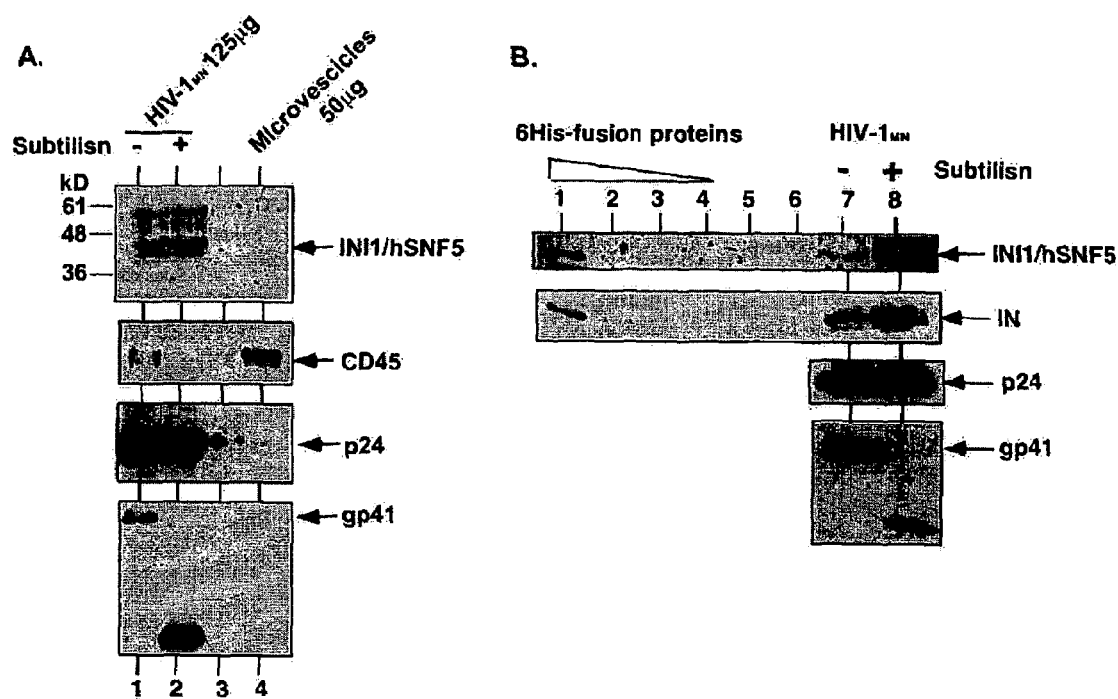
FIGS. 6A-6B. INI1/hSNF5 in the virions. A. Absence of INI1/hSNF5 in the purified microvesciclar frction. Lane 1, Untreated purified HIV-1MN virions; lane 2, Subtilisn treated purified HIV-1MN virions; lane 3, empty; lane 4, purified banded microvescicular fraction. Top panle, immunoblot probed with affinity purified −INI1 antibody; second panel from the top, probed with −CD45 antibody, third panel from the top, probed with −p24 antibody and the last panel, probed with—gp41 antibody. B. Stoichiometric analysis of IN:INI1/hSNF5 ratio in the virions. Lanes 1-4, Five-fold dilutions of normalization standards of partially purified 6His-INI1/hSNF5 (top panel) and 6His-IN (2nd panel); Lanes 5-6, empty; lanes 7, untreated HIV-1MN virions, lane 8 subtilisn treated HIV-1MN virions. First panel, probed with affinity purified −INI1 antibody, second panel probed with monoclonal −INI1 antibody; third panel, the same immunoblot probed with −gp41 antibody and the forth panel, probed with −p24 antibody.

Stiochimetry of INI1/hSNF5 in the HIV-1 virions and its absence in the microvescicular fractions. Previously we have demonstrated that purified HIV-1 virion particles treated with subtilisn incorporate INI1/hSNF5 protein. We further demonstrated that co-expression of haemagglutinin (HA)-tagged NI1/hSNF5 in the producer cells leads to the specific incorporation of HA-tagged INI1/hSNF5 into the purified and subtilisn-treated virions. It has been reported that even after two sucrose density gradient centrifugations and subtilisn treatment, the HIV-1 virion preparations may be contaminated with a low amount of microvescicles. Therefore, to conclusively demonstrate that the presence of INI1/hSNF5 in the virion preparations is not due to the microvesicular contamination, we examined and compared the proteins present in purified HIV-1MN virion preparations to that of the purified microvesicular fractions. For this purpose, total proteins from the purified fractions of microvesicles (~50 μg) along with purified HIV-1MN virions (125 μg) treated with subtilisn and purified on sucrose density gradients were separated on SDS/PAGE gel and were first subjected to immunoblot analysis using affinity purified anti-INI1/hSNF5 antibodies (FIG. 6A). While a clear distinct band corresponding to INI1/hSNF5 was detected in both subtilisn-treated and untreated HIV-1 virions, no band corresponding to INI1/hSNF5 was detected in the microvescicular fractions, even after longer exposure in repeated experiments (FIG. 6A). These results demonstrate that purified microvesicles are devoid of INI1/hSNF5.

To determine the amount of microvescicular contamination in the batch of HIV-1MN virions used in our experiments, we analyzed the presence of cellular proteins specific to the microvescicular fraction. It has been previously reported that one of the MHC Class II molecule, CD45, is specifically enriched in the microvescicular fractions and that it is not incorporated into HIV-1 particles. Therefore, we probed the above blot containing the microvescicles and HIV-1 with CD45 antibodies. As illustrated in FIG. 6A, the results indicated that while microvescicular fractions harbor abundant CD45, HIV-1 virions that were not treated with subtilisn harbor very low amounts of CD45, which was subsequently eliminated upon subtilisn digestion (FIG. 6A). Nevertheless, the virion preparations retained very similar amounts of INI1/hSNF5 regardless of the subtilisn treatment. Taken together, these results indicate that INI1/hSNF5 is clearly absent from microvescicular fractions and that the INI1/hSNF5 protein detected in the virion preparations is not due to microvescicular contamination.

Owing to the poor quality of α-INI1 antibodies available, a large amount of virion preparations were needed to detect INI1/hSNF5 in the above experiments, making it appear as though a very low amount of the protein is present in the virions. Therefore, to ascertain the exact amount of INI1/hSNF5 present in the virions, we determined the stoichiometry of IN:INI1/hSNF5 in these preparations. Since INI1/hSNF5 is likely to be incorporated by its association with HIV-1 IN, we surmised that INI1/hSNF5 protein will be present in the HIV-1 virions in similar molar amounts as compared to that of IN. For this purpose, we first purified recombinant hexahistidine tagged (6His) INI1/hSNF5 protein expressed in bacteria. The amount of full-length protein was quantitated against BSA standard and decreasing concentrations of the 6His-INI1/hSNF5 protein was loaded along with subtilisn-treated purified virion fractions. In the same lanes that contained 6His-INI1/hSNF5, we also included purified fractions of equimolar amounts of recombinant 6His-HIV-1 IN protein to determine the relative ratios of INI1 to IN within the virions.

The separated proteins were sequentially immunoblotted using affinity-purified antibodies against INI1/hSNF5 as well as antibodies against HIV-1 IN, p24, and gp41 (FIG. 6A). To avoid variation from experiment to experiment, and to be able to cross-compare the relative quantities of proteins in question within the same batch of purified virions, the blot was stripped and re-probed with different antibodies. The intensities of bands in the autoradiograms were subjected to quantitation using the ImageQuant. Table 3 illustrates our estimation of the approximate amount of IN and INI1 proteins present in the virion preparations compared to that of the standard. The results of this analysis indicated that molar ratios of IN:INI1/hSNF5 within the virions is approximately, 2:1 indicating a dimer of IN might bind to a monomer of INI1/hSNF5. Given that there are about 100 IN molecules per HIV-1 particle, we estimate that there are approximately 50 molecules of INI1/hSNF5 per virion particle.

TABLE 3

Stoichiometry of IN:INI1/hSNF5 in the virions.

| Protein | Mean Intensity Std | Protein Std | Mean Intensity Band 1 | Protein Band 1 | Mean Intensity Band 2 | Protein Band 2 | Avg intensity of bands | Avg Protein |
|---|---|---|---|---|---|---|---|---|
| IN | 5.0769 | 8.8 ng | 7.1433 | 12.38 ng | 9.6827 | 16.78 ng | 8.413 | 14.58 ng |
| INI/hSNF5 | 3.57 | 12.5 ng | 1.9905 | 6.97 ng | 4.5164 | 15.81 | 3.2535 | 11.39 ng |
| IN:INI1 ratio (ng) | | | | 1.77:1 | | 1.1:1 | | 1.3:1 |
| IN:INI1 molar ratio | | | | 2.3:1 | | 1.44:1 | | 1.7:1 |

Figure 7:
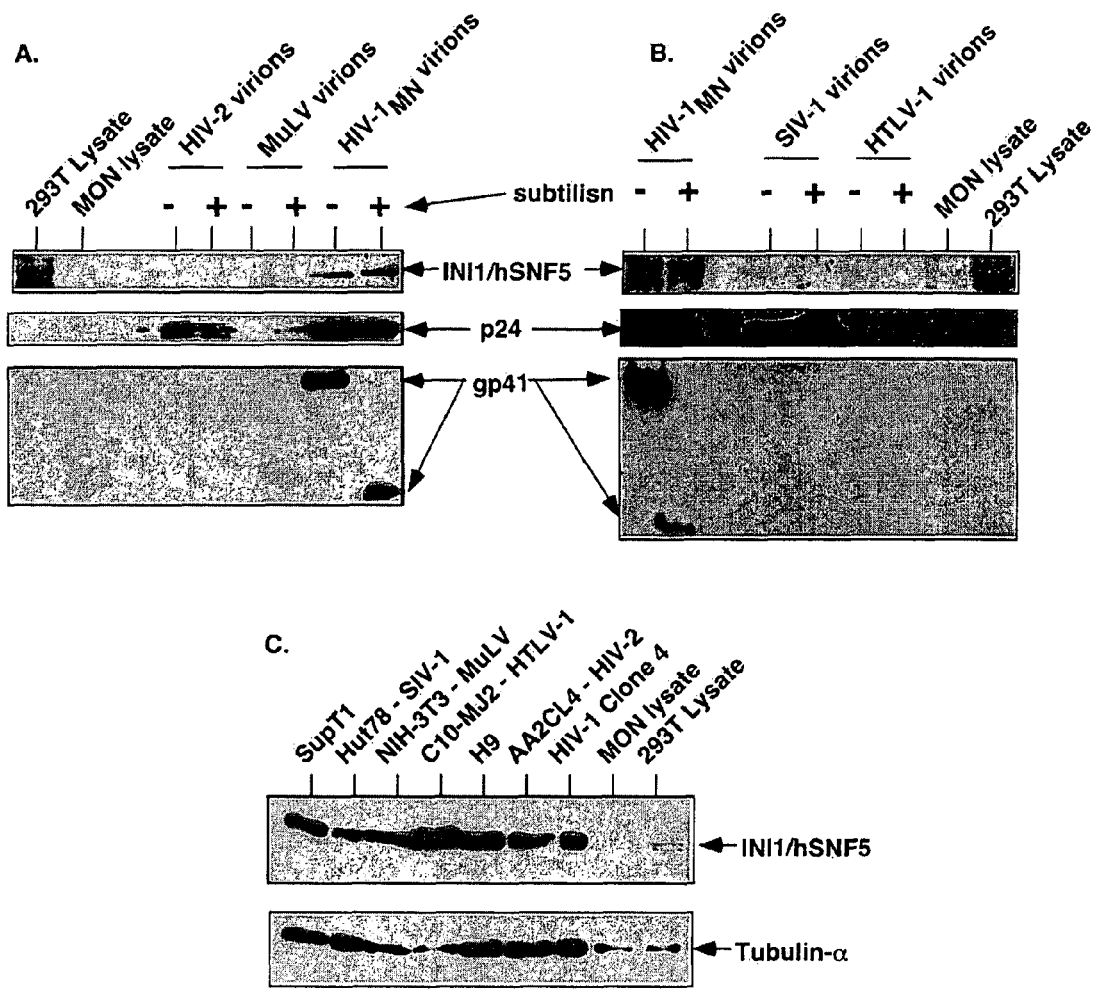
FIGS. 7A-7C. INI1/hSNF5 in various retrovirus particles. About 100 g each of purified and subtilisn-treated samples were loaded on to the gel along with the untreated controls. The blot was sequentially probed first with affinity purified −INI1 antibodies (top panel); then with −p24 antibodies (middle panel); and −gp41 antibodies (bottom panel). Panels include HIV-2, MULV and HIV-1 virions (panel A) and HIV-1, SIV and HTLV virions (panel B) along with total cell lysates from 293T (INI1+/+) and MON (INI1−/−) cells as control. Note the cross reactivity of −p24 antibodies to Capsid protein from HIV-1, HIV-2 and SIV-1. 2C., total cell lysates from various producer cells as indicated about the lanes. Top panel is probed with affinity purified −INI1 antibodies and the bottom panel represents the gel probed with −tubulin antibodies as loading control.

INI1 is specifically incorporated into HIV-1 but not into other related lentivirus particles. Once we confirmed the virion-specific association of INI1/hSNF5 in the particles and the lack of INI1 in the microvescicular fraction, we tested the specificity of incorporation of INI1 into various retrovirus particles. INI1/hSNF5 is a highly conserved protein and is documented to be present in all the eukaryotic species examined thus far. The conservation between mammalian proteins is very high, with primary amino acid sequence of human and mouse proteins being nearly 100% identical, except for one amino acid change. Therefore, we surmised that if INI1/hSNF5 is incorporated into other retrovirus particles, we should be able to detect them using the antibodies raised against human protein. To determine the specificity of incorporation of INI1/hSNF5 into various retroviruses, we generated purified virions from primate lentiviruses including HIV-1, HIV-2, SIVmac, HTLV-1 as well as a non-lentivirus such as MuLV. As before, the virions were prepared by banding the culture supernatants from the producer cells on sucrose gradients to eliminate the microvesicular fractions and treated with subtilisn to eliminate the contaminating proteins. These preparations were further purified on sucrose gradient and the total virion proteins were separated on SDS/PAGE and subjected to immunoblot analysis using antibodies to affinity purified α-INI1/hSNF5 antibodies. The results of these analyses illustrated that while a distinct band corresponding to INI1/hSNF5 was observed in lanes containing HIV-1 virions, no bands of similar size were apparent in lanes containing HIV-1, SIVmac, HTLV-1 or MuLV particles (FIG. 7). These results demonstrate that incorporation of INI1/hSNF5 is specific to HIV-1. The immunoblots were further treated with α-p24 (HIV-1), α-p30 (MULV) or α-gp41 antibodies to ensure comparable amount of loading in the subtilisn treated and untreated samples and to ensure complete digestion of the HIV-1 gp41 protein with subtilisn.

Since the virions used in this study were produced in different mammalian cell lines, the lack of incorporation of INI1/hSNF5 could be due to the lack of INI1/hSNF5 in these cells. To determine if sufficient amount of endogenous INI1/hSNF5 is expressed in these cell lines, we prepared lysates from H9, AA2CL4, Hut78, C10-MJ2 and NIH-3T3 cell lines that were used as producers for HIV-1, HIV-2, SIV-1, HTLV-1 and MuLV viruses respectively and subjected the total proteins from these cells for immunoblot analysis using affinity purified α-INI1/hSNF5 antibodies. As an internal control for the protein load, the blot was stripped and reprobed with α-tubulin antibodies. The results indicated that the producer cell lines used for the preparation of various retroviruses express sufficient quantities of INI1/hSNF5. These results indicate that lack of INI1/hSNF5 incorporation is not due to the lack of expression of INI1/hSNF5 protein in the producer cell lines.

Two-hybrid analysis to determine the protein-protein interaction of various retroviral integrases with INI1/hSNF5. Specific incorporation of INI1/hSNF5 into HIV-1 virions, despite the presence of endogenous INI1/hSNF5 in the producer cells, suggests that the incorporation is not due to the scooping effect but rather it is due to a specific, HIV-1 mediated mechanism. One possible mechanism by which this restricted incorporation is achieved is that the INI1/hSNF5 protein is recruited to HIV-1 virions by its ability to interact with HIV-1 IN and that it does not interact with integrases of other related retroviruses. Another cellular protein cyclophilin A, also has been demonstrated to exhibit specific interactions only with HIV-1 capsid but not with other related retroviruses. Interestingly CyPA is incorporated only into certain clades of HIV-1 and SIVCPZ and not into other retroviruses. To determine the specificity of interaction of INI1 with retroviral INs, we first examined the interaction of various INs with INI1/hSNF5 using the yeast two-hybrid system. Combinations of plasmids expressing LexADB and GAL4AC fusions of IN from HIV-1 (IN-1), HIV-2 (IN-2), SIVmac (IN-S), and HTLV-I (IN-T) and INI1/hSNF5 were co-expressed in yeast strain CTY10-5d carrying the LacZ gene as reporter for the two hybrid analysis. As negative controls, plasmids expressing various LexADB fusion proteins were transformed with plasmids expressing GAL4AC alone; and plasmids expressing all of the GAL4AC fusions were transformed with plasmids expressing LexADB alone. The transformants were stained with X-GAL to detect positive interactions between the various retroviral INs and INI1/hSNF5.

A compilation of the results obtained from multiple yeast transformations is presented in Table 4. The results demonstrate that co-expression of IN-1 and INI1/hSNF5 gave the strongest interactions when expressed as either of the two fusion proteins. The expression of LexADB fusions of IN-1 and IN-T along with GAL4AC resulted in white colonies. However, the remaining IN proteins gave low level of background activity. Both IN-2 and IN-S also demonstrated a weaker interaction with INI1/hSNF5. This interaction, however, was orientation dependent and was observed only when IN-2 and IN-S were fused to LexADB and not when fused to GAL4AC. Interestingly, IN-T, which is not closely related to IN-1, did not show any interaction with INI1 either as a LexADB or as GAL4AC fusion. The lack of interaction of IN-T with INI1/hSNF5 is not due to lack of protein expression or stability, as it's fusion protein exhibited homomeric interactions (data not shown). These results indicate that INI1/hSNF5 interacts strongly with HIV-1 IN but shows a weak interaction with HIV-2 and SIV Ins in the yeast two hybrid system.

TABLE 4

Interaction of various retroviral integrases with INI1/hSNF5

| LexA-DB fusion | GAL4AC fusions | β-Gal staining[a] |
|---|---|---|
| 1) LexA-DB | +GAL4AC | – |
| 2) LexADB-IN-1 | +GAL4AC | – |
| 3) LexADB-IN-2 | +GAL4AC | –/+ |
| 4) LexADB-IN-S | +GAL4AC | –/+ |
| 5) LexADB-IN-T | +GAL4AC | – |
| 6) LexADB | +GAL4AC-INI1/hSNF5 | – |
| 7) LexADB-IN-1 | +GAL4AC-INI1/hSNF5 | +++ |
| 8) LexADB-IN-2 | +GAL4AC-INI1/hSNF5 | + |
| 9) LexADB-IN-S | +GAL4AC-INI1/hSNF5 | + |
| 10) LexADB-IN-T | +GAL4AC-INI1/hSNF5 | – |
| 11) LexADB-INI1/hSNF5 | +GAL4AC | – |
| 12) LexADB-INI1/hSNF5 | +GAL4AC-IN-1 | +++ |
| 13) LexADB-INI1/hSNF5 | +GAL4AC-IN-2 | –/+ |
| 14) LexADB-INI1/hSNF5 | +GAL4AC-IN-S | –/+ |
| 15) LexADB-INI1/hSNF5 | +GAL4AC-IN-T | –/+ |
| 16) LexADB | +GAL4AC-IN-1 | – |
| 17) LexADB | +GAL4AC-IN-2 | – |
| 18) LexADB | +GAL4AC-IN-S | – |
| 19) LexADB | +GAL4AC-IN-T | – |

[a]"+++" = Strong interaction; blue staining visible within half an hour.
"+" = Weak interaction; blue staining visible within 2-3 hours.
"–/+" = Insignificant interaction; blue stain visible after 6-8 hours.
"–" = Negative interaction; No blue stain visible.

Figure 8:
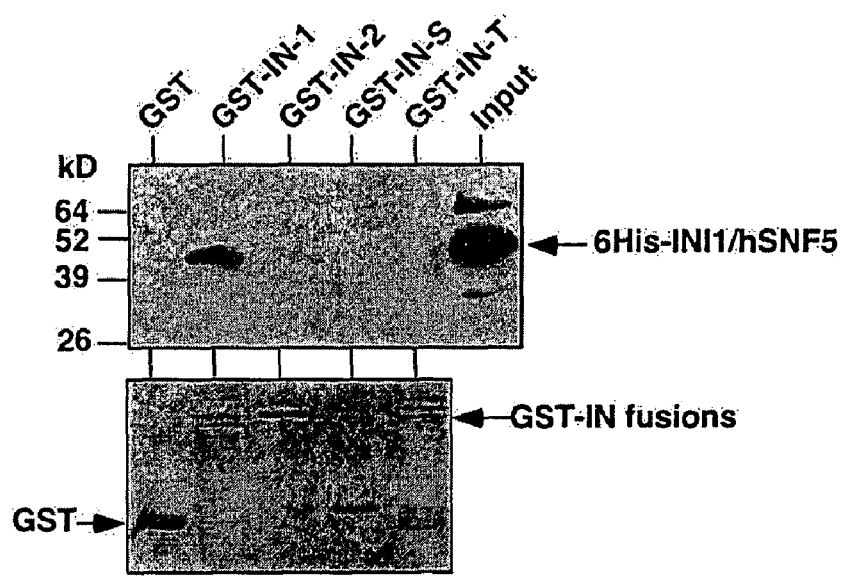
FIG. 8. The in vitro binding analysis to detect IN-INI1 interaction. GST and GST fusions of various integrases were incubated with bacterial lysates expressing 6His-IN-1. After the binding reaction, proteins were separated on SDS/PAGE and immunoblotted using anti-6His antibodies. Top panel, the label illustrates the binding reaction using the specified GST proteins. Note the pree coommassie stained gels of the binding reaction and panels B and D, immunoblot analysis of the duplicate gels of A and C. The GST and GST-fusion proteins used in the binding assay are indicated on the lanes. Positions of IN-1 and INI1 detected in the Western analysis are marked.

In vitro binding reaction to determine the direct protein-protein interactions of INs with INI1/hSNF5. The strong interaction in the yeast two hybrid system between HIV-1 IN and INI1/hSNF5 confirms the interaction between these two proteins. However, the weak interaction observed between IN-2, IN-S and INI1/hSNF5 could be due to the presence of bridging proteins. To clearly determine if these retroviral integrases have the ability to directly interact with INI1/hSNF5, we carried out in vitro interaction assays using GST-fusions of various integrases and the 6His-tagged bacterially expressed INI1/hSNF5 protein to confirm the finding in yeast two-hybrid system. We expressed various INs as fusions to GST and tested to see if they interacted with 6His-INI1/hSNF5 proteins in solution. The results of these in vitro interactions are illustrated in FIG. 7. The results of our analysis indicated that only the GST-IN-1 protein showed a distinct and strong interaction with 6His-INI1/hSNF5 (FIG. 8). None of the other proteins such as GST (a negative control), GST-IN-2, GST-IN-S or GST-IN-T displayed any interaction with INI1/hSNF5. The combined results from both the in vitro binding assays and yeast two-hybrid analysis indicate that INI1/hSNF5 specifically interacts with HIV-1 IN but not with other retroviral integrases. These results suggest that the weak interaction exhibited by IN-2 and IN-S in the two-hybrid system could be due to the presence of a bridging protein.

Specificity of inhibition of retroviral particle production by S6 transdominant mutant. Specific incorporation of INI1/hSNF5 into HIV-1 virion but not into other retrovirus particles is consistent with the observation that interaction of INI1/hSNF5 is restricted to HIV-1 IN. Previously we have demonstrated that a transdominant mutant of INI1/hSNF5, S6, strongly inhibits HIV-1 particle production. Furthermore, analysis of interaction-defective mutants suggests that the effect is due to the specific protein-protein interactions of S6 with IN-1 within the context of Gag-Pol. However, there is a possibility that S6 is inhibiting the assembly and particle production of HIV-1 by affecting the general cellular pathways needed for this process in an as yet undefined manner. To determine whether the S6 protein inhibits viral replication by blocking the viral replication in a general manner (a generic antiviral effect), or in a manner specific to HIV-1, we tested the effect of this transdominant mutant on the particle production of HIV-1R3B, HIV-2, SIVmac, HTLV-1, and MuLV. Full length DNA from the molecular clones of each of these viruses were transfected into 293T cells in the presence or absence of full-length HA-INI1 or HA-S6. Culture supernatants were obtained after 48 hours post-transfection, and the viral particle production monitored by assaying for RT activity. By producing the viruses via transfection with the full length molecular clones into 293T, a non-permissive cell line, we could eliminate the possibility of viral spread and isolate only the effects on a single round of viral production of each of the retroviruses.

Figure 9:
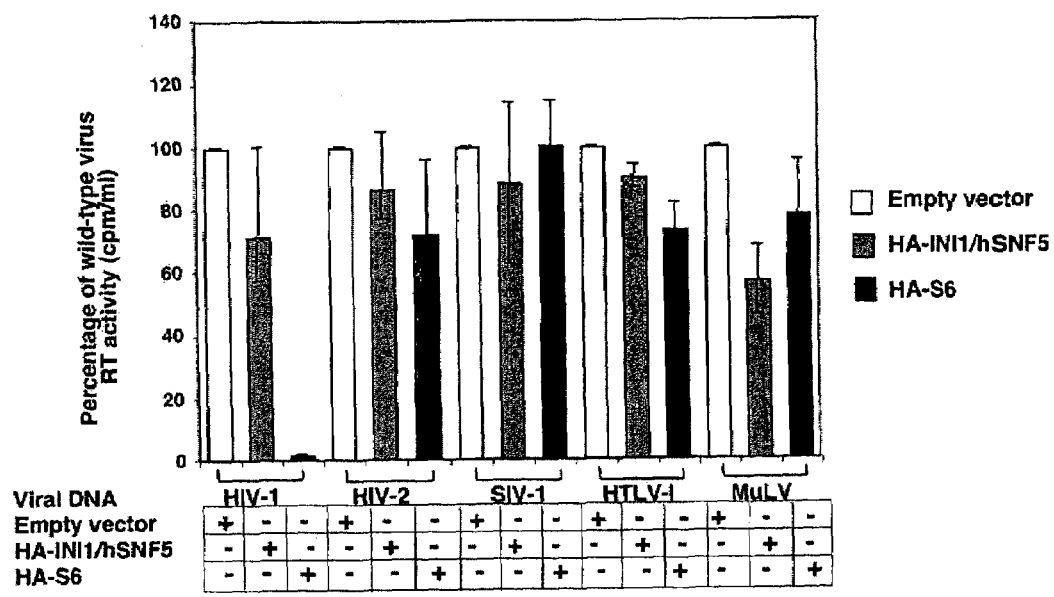
FIG. 9. Effect of S6 transdominant mutant of the particle production of various retroviruses. 293T cells were co-transfected with a full length molecular clones of HIV-1, HIV-2, SIV-1, HTLV-1 and MULV along with pCGN-S6 (expressing HA-S6), pCGN-INI1 (expressing HA-INI1), or an empty vector. The culture supernatants were assayed for RT activity to determine the amount of the virus produced in the supernatant.

The RT assay was carried out in buffer conditions that were optimal for each virus. For example, while the RT assay of HIV-1, HIV-2, HTLV-1 and SUV-1 were carried out in $Mg^{2+}$, the assay for MULV was carried out in $Mn^{2+}$. In each assay, the amount of virus produced in the absence of any other vector was arbitrarily set as 100% and amounts produced in the presence of INI1 or S6 were expressed as percentages of wild-type control viral production. We found that while the amount of HIV-1 virus is drastically reduced in the presence of S6, as previously reported, none of the other viruses were similarly affected (FIG. 9). We also found that over-expression of INI1 does not have significant effect on particle production of any of the retroviruses tested. These results indicated that the interaction between S6 and the retroviral integrases is a necessary mechanism by which S6 inhibits the viral particle production.

Discussion

In this report, we have examined the specificity and the stoichiometry of incorporation of INI1/hSNF5 into HIV-1 virion particles and determined the specificity of interaction of INI1/hSNF5 with various retroviral integrases. Comparison of purified microvesicular fractions to that of purified and subtilisn-treated virions indicate that while INI1/hSNF5 is completely absent from microvesicles, it is present in both subtilisn treated and untreated samples. Despite the lack of INI1/hSNF5 in the microvescicular fractions, we generally needed a large quantity of purified virions to clearly detect this protein in the particles, owing to the poor α-INI1/hSNF5 antibodies. However, stoichiometric analysis using purified 6His-INI1 antibodies suggests that approximately one molecule of INI1/hSNF5 is present for every two molecules of virion encapsidated IN. Considering that there are only about 100 molecules of IN per particles, this accounts to about 50 molecules of INI1/hSNF5 per particle, explaining the difficulty in detecting the protein readily by immunoblot analysis. It is important to note, at this point, that the interaction of CA allows the uptake of CyPA into HIV-1 virions, in roughly a 10:1 CA:CyPA ratio (Franke et al., 1994; Thali et al., 1994).

We further evaluated the specificity of incorporation of INI1/hSNF5 into various primate lentiviruses as well as MuLV. It appears that INI1/hSNF5 incorporation is restricted to HIV-1 and that even closely related retroviruses such as HIV-2 and SIV-1 do not incorporate INI1/hSNF5 despite the abundant presence of the protein in the producer cells. This observation suggests that a virus-specific mechanism is involved in this process. Our finding that INI1/hSNF5 interacts strongly and specifically with only HIV-1 in both yeast two hybrid system and IN the in vitro binding reactions lends support to the idea that it is recruited to HIV-1 virions by its direct interaction with IN.

Although yeast two hybrid studies indicate that the IN-S and IN-T proteins exhibit weak interactions with INI1/hSNF5, in one of the two orientations, the in vitro results indicate that none of the retroviral integrases (other than that of the HIV-1) were able to interact with INI1/hNSF5 suggesting that the INI1-interaction is very specific to HIV-1 IN. The specific interaction of INI1 with IN-1 opens the question of whether there are different interacting host proteins for other retroviral integrases. In addition, it raises the question as to why HIV-1 IN has evolved to interact with INI1/hSNF5 while other retroviruses do not incorporate this protein. It is possible that other retroviruses interact with cellular proteins that function in the same pathway as INI1/hSNF5. Or, perhaps it is possible that interaction of INI1/hSNF5 confers specific abilities to HIV-1 that is not achieved by other retroviruses. Isolation of host interacting proteins for other retroviral integrases may give us a better understanding of in vivo integration and host-virus interactions.

It is intriguing to note that although CyPA is required for normal HIV-1 replication kinetics, it is incorporated only into certain clades of HIV-1 and SIVCPZ and not into other retroviruses (Braaten and Lubin, 2001). Different lentiviral groups seem to be distinguishable by their differential incorporation of CyPA and requirement of CyPA for infectivity. HIV-1 group M incorporates CyPA and requires it for infectivity, HIV-2 and SIVcpz do not incorporate CyPA and do not require it for infectivity, and HIV-1 group O incorporates CyPA but does not require it for infectivity. Another protein that is demonstrated to interact with Gag protein during assembly is TSG101 (and its yeast homologue Vps23) that interact with late domain or the p6 protein of HIV-1 Gag. These proteins function in the sorting of proteins in the endosomal sorting pathway (Babst et al., 2000; Bishop and Woodman, 2000) and it is hypothesized that TSG101 may be a receptor for ubiquitinated proteins (such as mono-ubiquitinated Gag) that functions to select cargo proteins for incorporation into MVB (multivescicuclar bodies). It is interesting to note that while all the retroviruses appear to use various components of the MVB, there appear to be specificity and uniqueness with which each retrovirus use these pathways. While TSG101 directly interacts with HIV-1 late domain p6, it appear to not to interact with MULV Gag (Demirov et al., 2002). On the other hand, the Vps4 protein appears to directly bind MLV late domain (Garrus et al., 2001). Therefore, it is possible that similar to the specificity exhibited by the Gag-interacting proteins, the retroviral integrases could interact with various proteins functioning in the same pathway as that of INI1/hSNF5, and the viruses might exhibit differential ability to incorporate these proteins into the virus.

In this report, we also have demonstrated that the ability of retroviral INs to interact with INI1/hSNF5 correlates with the specificity of inhibition of particle production by the INI1/hSNF5 derived trans-dominant mutant, S6. We found that while S6 strongly inhibits particle production of HIV-1 in 293T cells, it does not inhibit the particle production of other retroviruses including HIV-2, SIV-1, HTLV-I and MuLV in the same cells. This result clearly illustrates the fact that S6 does not inhibit the particle production by blocking certain cellular pathway necessary for the particle production of retroviruses but rather, it indicates that S6 mediates its effect by its direct interaction with HIV-1 IN. We believe that this highly specific and potent inhibition is of tremendous value in developing strategies to control HIV-1 replication. Isolation of drugs that precisely mimic the specificity and potency of S6 may be therapeutically useful in preventing the re-emergence of viruses from latently infected pools. Finally, inhibition of HIV-1 particle production by S6 precludes the use of lentiviruses for gene therapy strategies to deliver S6 into hematopoitic stem cells to prevent HIV-1 replication. Based on our results, we propose that either the use of other lentivirus based vectors such as those derived from HIV-2, or chimeric HIV-1-based vectors harboring integrase sequences from other retroviruses will be valuable for this purpose.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NO:'s

SEQ ID NO:1 - INI1/hSNF5 amino acid sequence.
GenBank U04847

```
  1 MMMMALSKTF GQKPVKFQLE DDGEFYMIGS EVGNYLRMFR
 41 GSLYKRYPSL WRRLATVEER KKIVASSHGK KTKPNTKDHG
 81 YTTLATSVTL LKASEVEEIL DGNDEKYKAV SISTEPPTYL
121 REQKAKRNSQ WVPTLSNSSH HLDAVPCSTT INRNRMGRDK
161 KRTFPLCFDD HDPAVIHENA SQPEVLVPIR LDMEIDGQKL
201 RDAFTWNMNE KLMTPEMFSE ILCDDLDLNP LTFVPAIASA
241 IRQQIESYPT DSILEDQSDQ RVIIKLNIHV GNISLVDQFE
281 WDMSEKENSP EKFALKLCSE LGLGGEFVTT IAYSIRGQLS
321 WHQKTYAFSE NPLPTVEIAI RNTGDADQWC PLLETLTDAE
361 MEKKIRDQDR NTRRMRRLAN TGPAW
```

SEQ ID NO:2 - Rpt1 of INI1/hSNF5 (aa 183-245)

PEVLVPIRLDMEIDGQKLRDAFTWNMNEKLMTPEMFSEILCDDLDLNPLT
FVPAIASAIRQQI

SEQ ID NO:3 - s6 fragment of INI1/hSNF5 (aa 183-294)

PEVLVPIRLDMEIDGQKLRDAFTWNMNEKLMTPEMFSEILCDDLDLNPLT
FVPAIASAIRQQIESYPTDSILEDQSDQRVIIKLNIHVGNISLVDQFEWD
MSEKENSPEKFA

SEQ ID NO:4 - 27b fragment of INI1/hSNF5 (aa 1-245)

```
  1 MMMMALSKTF GQKPVKFQLE DDGEFYMIGS EVGNYLRMFR
 41 GSLYKRYPSL WRRLATVEER KKIVASSHGK KTKPNTKDHG
 81 YTTLATSVTL LKASEVEEIL DGNDEKYKAV SISTEPPTYL
121 REQKAKRNSQ WVPTLSNSSH HLDAVPCSTT INRNRMGRDK
161 KRTFPLCFDD HDPAVIHENA SQPEVLVPIR LDMEIDGQKL
201 RDAFTWNMNE KLMTPEMFSE ILCDDLDLNP LTFVPAIASA
241 IRQQI
```

SEQ ID NO:5 - 20.2 fragment of INI1/hSNF5 (aa 141-385)

HLDAVPCSTTINRNRMGRDKKRTFPLCFDDHDPAVIHENASQPEVLVPIR
LDMEIDGQKLRDAFTWNMNEKLMTPEMFSEILCDDLDLNPLTFVPAIASA
IRQQIESYPTDSILEDQSDQRVIIKLNIHVGNISLVDQFEWDMSEKENSP
EKFALKLCSELGLGGEFVTTIAYSIRGQLSWHQKTYAFSENPLPTVEIAI
RNTGDADQWCPLLETLTDAEMEKKIRDQDRNTRRMRRLANTGPAW

SEQ ID NO:6 - cDNA sequence of INI1/hSNF5 GenBank U04847

```
  1 gccccggccc cgccccagcc ctcctgatcc ctcgcagccc
    ggctccggcc gcccgcctct
 61 gccgccgcaa tgatgatgat ggcgctgagc aagaccttcg
    ggcagaagcc cgtgaagttc
121 cagctggagg acgacggcga gttctacatg atcggctccg
    aggtgggaaa ctacctccgt
181 atgttccgag gttctctgta caagagatac ccctcactct
    ggaggcgact agccactgtg
241 gaagagagga agaaaatagt tgcatcgtca catggtaaaa
    aaacaaaacc taacactaag
301 gatcacggat acacgactct agccaccagt gtgaccctgt
    taaaagcctc ggaagtggaa
361 gagattctgg atggcaacga tgagaagtac aaggctgtgt
    ccatcagcac agagcccccc
421 acctacctca gggaacagaa ggccaagagg aacagccagt
    gggtacccac cctgtccaac
```

APPENDIX-continued

SEQ ID NO's

```
 481 agctcccacc acttagatgc cgtgccatgc tccacaacca
     tcaacaggaa ccgcatgggc 541 cgagacaaga agagaacctt cccccctttgc tttgatgacc
     atgacccagc tgtgatccat 601 gagaacgcat ctcagcccga ggtgctggtc cccatccggc
     tggacatgga gatcgatggg 661 cagaagctgc gagacgcctt cacctggaac atgaatgaga
     agttgatgac gcctgagatg 721 ttttcagaaa tcctctgtga cgatctggat ttgaacccgc
     tgacgtttgt gccagccatc 781 gcctctgcca tcagacagca gatcgagtcc taccccacgg
     acagcatcct ggaggaccag 841 tcagaccagc gcgtcatcat caagctgaac atccatgtgg
     gaaacatttc cctggtggac 901 cagtttgagt gggacatgtc agagaaggag aactcaccag
     agaagtttgc cctgaagctg 961 tgctcggagc tggggttggg cggggagttt gtcaccacca
     tcgcatacag catccgggga 1021 cagctgagct ggcatcagaa gacctacgcc ttcagcgaga
     accctctgcc cacagtggag 1081 attgccatcc ggaacacggg cgatgcggac cagtggtgcc
     cactgctgga gactctgaca 1141 gacgctgaga tggagaagaa gatccgcgac caggacagga
     acacgaggcg gatgaggcgt 1201 cttgccaaca cgggccccgc ctggtaacca gcccatcagc
     acacggctcc cacggagcat 1261 ctcagaagat tgggccgcct ctcctccatc ttctggcaag
     gacagaggcg agggacagc 1321 ccagcgccat cctgaggatc gggtgggggt ggagtggggg
     cttccaggtg gcccttcccg 1381 gtacacattc catttgttga gccccagtcc tgccccccac
     cccaccctcc ctacccctcc 1441 ccagtctctg gggtcaggaa gaaacccttat tttaggttgt
     gttttgtttt tgtataggag 1501 ccccaggcag ggctagtaac agttttttaaa taaaaggcaa
     caggtcatgt tcaatttctt 1561 aaatctagtg tctttatttc ttctgttaca atagtgttgc
     ttgtgtaagc aggttagagt 1621 gcacagtgtc cccaattgtt cctggcactg caaaaccaaa
     ttaaacaatc ccacaaagaa 1681 ttctgacatc aatgtgtttt cctcagtcag gtctatttca
     agattctaga agttccttt 1741 gtaaaacttg cctttaaaac tcttcctcct aatgccatca
     gatctcttaa cattggctca 1801 ctgtgggatc tttcctctta ggttgaattt ctacgtgaat
     atcaaagtgc cttttc
```

APPENDIX-continued

SEQ ID NO's

SEQ ID NO:7 - primer EC2

CCGCTCTAGATCAACCGAGGGC

SEQ ID NO:8 - primer EC7

CGAATTCCGGATGCGCGAGCCC

SEQ ID NO:9 - S6 mutant E3 -
mutated amino acid residue underlined

PEVLVPIRLDMEIDGQKLRDAFTWNMNEKLMTPEMFSEILCGDLDLNPLT

FVPAIASAIRQQIESYPTDSILEDQSDQRVIIKLNIHVGNISLVDQFEWD

MSEKENSPEKFA

SEQ ID NO:10 - S6 mutant E4 -
mutated amino acid residue underlined

PEVLVPIRLDMEIDGQKLRDAFTWNMNEKLMAPEMFSEILCDDLDLNPLT

FVPAIASAIRQQIESYPTDSILEDQSDQRVIIKLNIHVGNISLVDQFEWD

MSEKENSPEKFA

SEQ ID NO:11 - S6 mutant E7 -
mutated amino acid residue underlined

PEVLVPIRIDMEIDGQKLRDAFTWNMNEKLMTPEMFSEILCDDLDLNPLT

FVPAIASAIRQQIEPYPTDSILEDQSDQRVIIKLNIHVGNISLVDQFEWD

MSEKENSPEKFA

SEQ ID NO:12 - S6 mutant E10 -
mutated amino acid residue underlined

PEVLVPIRLDMEIDGQKLRDAFTWNMNEKLMTPEMFSEILCDDLGLNPLT

FVPAIASAIRQQIESYPTDSILEDQSDQRVIIKLNIHVGNISLVDQFEWD

MSEKENSPEKFA

SEQ ID NO:13 - GKSIV-A primer

CGCGGATCCTCTTCTTGGAAAAGATAGAGCCA)

SEQ ID NO:14 - GKSIV-C primer

CGGAATTCCTATGCCACCTCTCTAGA

SEQ ID NO:15 - GKHIV2-A primer

CGCGGATCCTGTTCCTGGAAAAAATAGAG

SEQ ID NO:16 - GKHIV2-C primer

CGGAATTCTATGCCATTTCTCCATCC

SEQ ID NO:17 - HTLV-1F primer

CGGAATTCGTCCTGCAGCTC

SEQ ID NO:18 - HTLV-1R primer

GCGAATTCTTACCCATGGTG

What is claimed is:

1. A purified peptide comprising an Rpt1 domain of an INI1/hSNF5, the Rpt1 domain having the sequence of SEQ ID NO:2, wherein the peptide inhibits HIV-1 virion production in a human cell and wherein the peptide consists of SEQ ID NO:5 or is a fragment of SEQ ID NO:5.

2. The peptide of claim 1, further comprising an amino acid sequence not found in INI1/hSNF5.

3. The peptide of claim 1, further comprising a non-peptide moiety.

4. The peptide of claim 1, wherein the peptide does not further comprise a non-peptide moiety.

5. The peptide of claim 1, wherein the human cell is a T cell.

6. The peptide of claim 1, comprising SEQ ID NO:3.

7. The peptide of claim 6, consisting of SEQ ID NO:3.

8. The peptide of claim 1, wherein the pevtide is a fragment of SEQ ID NO:3.

9. A cell in vitro comprising the peptide of claim 1.

10. The cell of claim 9, wherein the cell is a human cell.

11. The cell of claim 9, wherein the cell is a hematopoietic stem cell.

12. The cell of claim 9, wherein the cell is a T cell.

13. The cell of claim 9, wherein the cell is infected with HIV-1.

14. The cell of claim 9, wherein the peptide is present in an amount sufficient to inhibit replication or virion production of HIV-1 in the cell, or spread of HIV-1 to another cell.

15. The cell of claim 9, wherein the cell expresses the peptide.

16. A vector encoding the peptide of claim 4, wherein the peptide is expressed in a human cell when the cell is transfected with the vector.

17. The vector of claim 16 wherein, when the cell is transfected with the vector, the peptide is expressed in amounts sufficient to inhibit replication or virion production of HIV-1 in the cell, or spread of HIV-1 to another cell.

18. An isolated or cultured human cell transfected with the vector of claim 16.

19. The cell of claim 18, wherein the peptide is expressed in amounts sufficient to inhibit replication or virion production of HIV-1 in the cell, or spread of HIV-1 to another cell.

20. The peptide of claim 1, formulated in a composition that facilitates entry of the peptide into a cell.

21. The cell of claim 18, wherein the cell is infected with HIV-1.

* * * * *

SEQUENCE LISTING

<160> NUMBER OF SEQ ID NOS: 18

<210> SEQ ID NO 1
<211> LENGTH: 385
<212> TYPE: PRT
<213> ORGANISM: Homo sapiens

<400> SEQUENCE: 1

```
Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Ser Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
                245                 250                 255

Gln Ser Asp Gln Arg Val Ile Ile Lys Leu Asn Ile His Val Gly Asn
            260                 265                 270

Ile Ser Leu Val Asp Gln Phe Glu Trp Asp Met Ser Glu Lys Glu Asn
        275                 280                 285

Ser Pro Glu Lys Phe Ala Leu Lys Leu Cys Ser Glu Leu Gly Leu Gly
    290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
            340                 345                 350

Leu Glu Thr Leu Thr Asp Ala Glu Met Glu Lys Lys Ile Arg Asp Gln
```

```
                355                 360                 365
Asp Arg Asn Thr Arg Arg Met Arg Arg Leu Ala Asn Thr Gly Pro Ala
    370                 375                 380

Trp
385

<210> SEQ ID NO 2
<211> LENGTH: 63
<212> TYPE: PRT
<213> ORGANISM: Homo sapiens

<400> SEQUENCE: 2

Pro Glu Val Leu Val Pro Ile Arg Leu Asp Met Glu Ile Asp Gly Gln
1               5                   10                  15

Lys Leu Arg Asp Ala Phe Thr Trp Asn Met Asn Glu Lys Leu Met Thr
            20                  25                  30

Pro Glu Met Phe Ser Glu Ile Leu Cys Asp Asp Leu Asp Leu Asn Pro
        35                  40                  45

Leu Thr Phe Val Pro Ala Ile Ala Ser Ala Ile Arg Gln Gln Ile
    50                  55                  60

<210> SEQ ID NO 3
<211> LENGTH: 112
<212> TYPE: PRT
<213> ORGANISM: Homo sapiens

<400> SEQUENCE: 3

Pro Glu Val Leu Val Pro Ile Arg Leu Asp Met Glu Ile Asp Gly Gln
1               5                   10                  15

Lys Leu Arg Asp Ala Phe Thr Trp Asn Met Asn Glu Lys Leu Met Thr
            20                  25                  30

Pro Glu Met Phe Ser Glu Ile Leu Cys Asp Asp Leu Asp Leu Asn Pro
        35                  40                  45

Leu Thr Phe Val Pro Ala Ile Ala Ser Ala Ile Arg Gln Gln Ile Glu
    50                  55                  60

Ser Tyr Pro Thr Asp Ser Ile Leu Glu Asp Gln Ser Asp Gln Arg Val
65                  70                  75                  80

Ile Ile Lys Leu Asn Ile His Val Gly Asn Ile Ser Leu Val Asp Gln
                85                  90                  95

Phe Glu Trp Asp Met Ser Glu Lys Glu Asn Ser Pro Glu Lys Phe Ala
            100                 105                 110

<210> SEQ ID NO 4
<211> LENGTH: 245
<212> TYPE: PRT
<213> ORGANISM: Homo sapiens

<400> SEQUENCE: 4

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80
```

```
Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Ser Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile
                245

<210> SEQ ID NO 5
<211> LENGTH: 245
<212> TYPE: PRT
<213> ORGANISM: Homo sapiens

<400> SEQUENCE: 5

His Leu Asp Ala Val Pro Cys Ser Thr Thr Ile Asn Arg Asn Arg Met
1               5                   10                  15

Gly Arg Asp Lys Lys Arg Thr Phe Pro Leu Cys Phe Asp Asp His Asp
            20                  25                  30

Pro Ala Val Ile His Glu Asn Ala Ser Gln Pro Glu Val Leu Val Pro
        35                  40                  45

Ile Arg Leu Asp Met Glu Ile Asp Gly Gln Lys Leu Arg Asp Ala Phe
    50                  55                  60

Thr Trp Asn Met Asn Glu Lys Leu Met Thr Pro Glu Met Phe Ser Glu
65                  70                  75                  80

Ile Leu Cys Asp Asp Leu Asp Leu Asn Pro Leu Thr Phe Val Pro Ala
                85                  90                  95

Ile Ala Ser Ala Ile Arg Gln Gln Ile Glu Ser Tyr Pro Thr Asp Ser
            100                 105                 110

Ile Leu Glu Asp Gln Ser Asp Gln Arg Val Ile Ile Lys Leu Asn Ile
        115                 120                 125

His Val Gly Asn Ile Ser Leu Val Asp Gln Phe Glu Trp Asp Met Ser
    130                 135                 140

Glu Lys Glu Asn Ser Pro Glu Lys Phe Ala Leu Lys Leu Cys Ser Glu
145                 150                 155                 160

Leu Gly Leu Gly Gly Glu Phe Val Thr Thr Ile Ala Tyr Ser Ile Arg
                165                 170                 175

Gly Gln Leu Ser Trp His Gln Lys Thr Tyr Ala Phe Ser Glu Asn Pro
            180                 185                 190

Leu Pro Thr Val Glu Ile Ala Ile Arg Asn Thr Gly Asp Ala Asp Gln
```

```
                195                 200                 205
            Trp Cys Pro Leu Leu Glu Thr Leu Thr Asp Ala Glu Met Glu Lys Lys
                210                 215                 220

Ile Arg Asp Gln Asp Arg Asn Thr Arg Arg Met Arg Arg Leu Ala Asn
            225                 230                 235                 240

Thr Gly Pro Ala Trp
                        245

<210> SEQ ID NO 6
<211> LENGTH: 1857
<212> TYPE: DNA
<213> ORGANISM: Homo sapiens

<400> SEQUENCE: 6
gccccggccc cgccccagcc ctcctgatcc ctcgcagccc ggctccggcc gcccgcctct       60
gccgccgcaa tgatgatgat ggcgctgagc aagaccttcg ggcagaagcc cgtgaagttc      120
cagctggagg acgacggcga gttctacatg atcggctccg aggtgggaaa ctacctccgt      180
atgttccgag gttctctgta caagagatac ccctcactct ggaggcgact agccactgtg      240
gaagagagga agaaaatagt tgcatcgtca catggtaaaa aaacaaaacc taacactaag      300
gatcacggat acacgactct agccaccagt gtgaccctgt aaaagcctc ggaagtggaa       360 gagattctgg atggcaacga tgagaagtac aaggctgtgt ccatcagcac agagcccccc      420
acctacctca gggaacagaa ggccaagagg aacagccagt gggtacccac cctgtccaac      480
agctcccacc acttagatgc cgtgccatgc tccacaacca tcaacaggaa ccgcatgggc      540
cgagacaaga agagaacctt cccccttttgc tttgatgacc atgacccagc tgtgatccat      600
gagaacgcat ctcagcccga ggtgctggtc cccatccggc tggacatgga gatcgatggg      660
cagaagctgc gagacgcctt cacctggaac atgaatgaga agttgatgac gcctgagatg      720
ttttcagaaa tcctctgtga cgatctggat ttgaacccgc tgacgtttgt gccagccatc      780
gcctctgcca tcagacagca gatcgagtcc tacccacgg acagcatcct ggaggaccag      840
tcagaccagc gcgtcatcat caagctgaac atccatgtgg aaacatttc cctggtggac      900 cagtttgagt gggacatgtc agagaaggag aactcaccag agaagtttgc cctgaagctg      960
tgctcggagc tggggttggg cgggagtttt gtcaccacca tcgcatacag catccgggga     1020
cagctgagct ggcatcagaa gacctacgcc ttcagcgaga accctctgcc cacagtggag     1080
attgccatcc ggaacacggg cgatgcggac cagtggtgcc cactgctgga gactctgaca     1140
gacgctgaga tggagaagaa gatccgcgac caggacagga cacgaggcg gatgaggcgt      1200 cttgccaaca cgggccccggc ctggtaacca gccatcagc acacggctcc cacggagcat     1260
ctcagaagat tgggccgcct ctcctccatc ttctggcaag gacagaggcg aggggacagc     1320
ccagcgccat cctgaggatc gggtgggggt ggagtggggg cttccaggtg gcccttcccg     1380
gtacacattc catttgttga gccccagtcc tgcccccac cccacccctcc ctaccctcc      1440 ccagtctctg gggtcaggaa gaaaccttat tttaggttgt gttttgtttt tgtataggag     1500
ccccaggcag ggctagtaac agttttaaa taaaaggcaa caggtcatgt tcaatttctt      1560
aaatctagtg tctttatttc ttctgttaca atagtgttgc ttgtgtaagc aggttagagt     1620
gcacagtgtc cccaattgtt cctggcactg caaaccaaa ttaaacaatc ccacaaagaa      1680
ttctgacatc aatgtgtttt cctcagtcag gtctatttca agattctaga agttccttt     1740 gtaaaacttg cctttaaaac tcttcctcct aatgccatca gatctcttaa cattggctca     1800
```

```
ctgtgggatc tttcctctta ggttgaattt ctacgtgaat atcaaagtgc ctttttc      1857
```

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7

```
ccgctctaga tcaaccgagg gc                                              22
```

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8

```
cgaattccgg atgcgcgagc cc                                              22
```

<210> SEQ ID NO 9
<211> LENGTH: 112
<212> TYPE: PRT
<213> ORGANISM: Homo sapiens

<400> SEQUENCE: 9

```
Pro Glu Val Leu Val Pro Ile Arg Leu Asp Met Glu Ile Asp Gly Gln
1               5                   10                  15

Lys Leu Arg Asp Ala Phe Thr Trp Asn Met Asn Glu Lys Leu Met Thr
            20                  25                  30

Pro Glu Met Phe Ser Glu Ile Leu Cys Gly Asp Leu Asp Leu Asn Pro
        35                  40                  45

Leu Thr Phe Val Pro Ala Ile Ala Ser Ala Ile Arg Gln Gln Ile Glu
    50                  55                  60

Ser Tyr Pro Thr Asp Ser Ile Leu Glu Asp Gln Ser Asp Gln Arg Val
65                  70                  75                  80

Ile Ile Lys Leu Asn Ile His Val Gly Asn Ile Ser Leu Val Asp Gln
                85                  90                  95

Phe Glu Trp Asp Met Ser Glu Lys Glu Asn Ser Pro Glu Lys Phe Ala
            100                 105                 110
```

<210> SEQ ID NO 10
<211> LENGTH: 112
<212> TYPE: PRT
<213> ORGANISM: Homo sapiens

<400> SEQUENCE: 10

```
Pro Glu Val Leu Val Pro Ile Arg Leu Asp Met Glu Ile Asp Gly Gln
1               5                   10                  15

Lys Leu Arg Asp Ala Phe Thr Trp Asn Met Asn Glu Lys Leu Met Ala
            20                  25                  30

Pro Glu Met Phe Ser Glu Ile Leu Cys Asp Asp Leu Asp Leu Asn Pro
        35                  40                  45

Leu Thr Phe Val Pro Ala Ile Ala Ser Ala Ile Arg Gln Gln Ile Glu
    50                  55                  60

Ser Tyr Pro Thr Asp Ser Ile Leu Glu Asp Gln Ser Asp Gln Arg Val
65                  70                  75                  80

Ile Ile Lys Leu Asn Ile His Val Gly Asn Ile Ser Leu Val Asp Gln
```

```
                        85                  90                  95

Phe Glu Trp Asp Met Ser Glu Lys Glu Asn Ser Pro Glu Lys Phe Ala
            100                 105                 110

<210> SEQ ID NO 11
<211> LENGTH: 112
<212> TYPE: PRT
<213> ORGANISM: Homo sapiens

<400> SEQUENCE: 11

Pro Glu Val Leu Val Pro Ile Arg Leu Asp Met Glu Ile Asp Gly Gln
1               5                   10                  15

Lys Leu Arg Asp Ala Phe Thr Trp Asn Met Asn Glu Lys Leu Met Thr
            20                  25                  30

Pro Glu Met Phe Ser Glu Ile Leu Cys Asp Asp Leu Asp Leu Asn Pro
        35                  40                  45

Leu Thr Phe Val Pro Ala Ile Ala Ser Ala Ile Arg Gln Gln Ile Glu
    50                  55                  60

Pro Tyr Pro Thr Asp Ser Ile Leu Glu Asp Gln Ser Asp Gln Arg Val
65                  70                  75                  80

Ile Ile Lys Leu Asn Ile His Val Gly Asn Ile Ser Leu Val Asp Gln
                85                  90                  95

Phe Glu Trp Asp Met Ser Glu Lys Glu Asn Ser Pro Glu Lys Phe Ala
            100                 105                 110

<210> SEQ ID NO 12
<211> LENGTH: 112
<212> TYPE: PRT
<213> ORGANISM: Homo sapiens

<400> SEQUENCE: 12

Pro Glu Val Leu Val Pro Ile Arg Leu Asp Met Glu Ile Asp Gly Gln
1               5                   10                  15

Lys Leu Arg Asp Ala Phe Thr Trp Asn Met Asn Glu Lys Leu Met Thr
            20                  25                  30

Pro Glu Met Phe Ser Glu Ile Leu Cys Asp Asp Leu Gly Leu Asn Pro
        35                  40                  45

Leu Thr Phe Val Pro Ala Ile Ala Ser Ala Ile Arg Gln Gln Ile Glu
    50                  55                  60

Ser Tyr Pro Thr Asp Ser Ile Leu Glu Asp Gln Ser Asp Gln Arg Val
65                  70                  75                  80

Ile Ile Lys Leu Asn Ile His Val Gly Asn Ile Ser Leu Val Asp Gln
                85                  90                  95

Phe Glu Trp Asp Met Ser Glu Lys Glu Asn Ser Pro Glu Lys Phe Ala
            100                 105                 110

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
cgcggatcct cttcttggaa aagatagagc ca                              32

<210> SEQ ID NO 14
<211> LENGTH: 26
<212> TYPE: DNA
```

```
<213> ORGANISM: Artificial Sequence
<220> FEATURE:
<223> OTHER INFORMATION: primer

<400> SEQUENCE: 14
cggaattcct atgccacctc tctaga                                           26

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
cgcggatcct gttcctggaa aaatagag                                         29

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
cggaattcta tgccatttct ccatcc                                           26

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
cggaattcgt cctgcagctc                                                  20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gcgaattctt acccatggtg                                                  20
```